(12) United States Patent
Ninomiya et al.

(10) Patent No.: US 8,244,326 B2
(45) Date of Patent: Aug. 14, 2012

(54) PROBE DEVICE

(75) Inventors: Atsushi Ninomiya, Ome (JP); Yoshimi Kasai, Kokubunji (JP); Yukiko Hirabayashi, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 1259 days.

(21) Appl. No.: 11/940,341

(22) Filed: Nov. 15, 2007

(65) Prior Publication Data

US 2008/0183055 A1 Jul. 31, 2008

(30) Foreign Application Priority Data

Dec. 27, 2006 (JP) .................................. 2006-350850

(51) Int. Cl.
*A61B 5/1455* (2006.01)
(52) U.S. Cl. ......... 600/344; 600/310; 600/322; 600/323
(58) Field of Classification Search .................. 600/309, 600/310, 322, 338, 344, 383, 323, 324, 340
See application file for complete search history.

(56) References Cited

U.S. PATENT DOCUMENTS

| | | | |
|---|---|---|---|
| 4,510,938 A * | 4/1985 | Jobsis et al. ................... | 600/344 |
| 5,038,782 A | 8/1991 | Gevins et al. | |
| 5,497,771 A * | 3/1996 | Rosenheimer ................ | 600/323 |
| 5,529,065 A * | 6/1996 | Tsuchiya ..................... | 600/310 |
| 6,201,982 B1 | 3/2001 | Menkes et al. | |
| 2002/0029005 A1* | 3/2002 | Levendowski et al. ........ | 600/383 |
| 2004/0054271 A1 | 3/2004 | Maki et al. | |

FOREIGN PATENT DOCUMENTS

| | | |
|---|---|---|
| JP | 2001-286449 | 10/2001 |
| WO | WO00/45701 | 8/2000 |

* cited by examiner

*Primary Examiner* — Eric Winakur
*Assistant Examiner* — Chu Chuan (JJ) Liu
(74) *Attorney, Agent, or Firm* — Antonelli, Terry, Stout & Kraus, LLP.

(57) ABSTRACT

A probe device for optically measuring a condition of an object includes a light emitter for emitting a light to proceed into the object through a surface of the object, a light sensor for measuring an optical condition of the light proceeding from the surface through the object and subsequently emitted from the surface to reach the light sensor, and a body holding thereon at least one of the light emitter and the light sensor. The body includes at least one main protrusion protruding so as to face to the surface, and at least two sub-protrusions arranged around the at least one main protrusion and protruding so as to face to the surface.

18 Claims, 15 Drawing Sheets

FIG. 17A
FIG. 17B
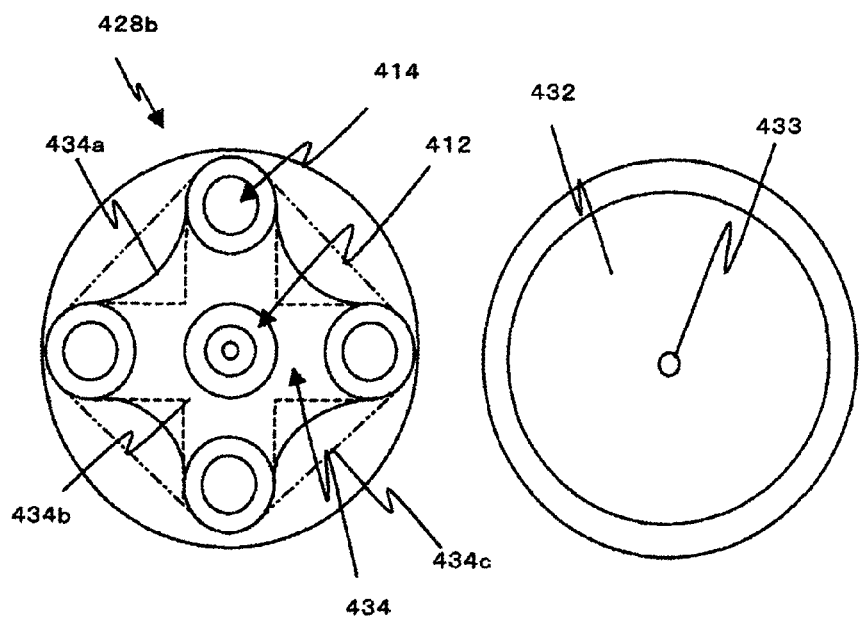
FIG. 17C
FIG. 17D
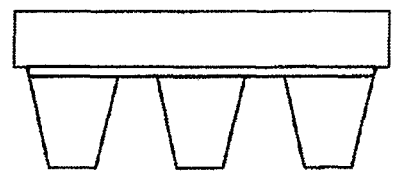

PROBE DEVICE

INCORPORATION BY REFERENCE

The present application claims priority from Japanese application JP2006-350850 filed on Dec. 27, 2006, the content of which is hereby incorporated by reference into this application.

BACKGROUND OF THE INVENTION

The present invention relates to a probe device for a biological optical measurement device, and more particularly, to a probe device for a biological optical measurement device suitably applicable to measurement of local hemodynamic variations in a living body.

A measurement device called an "optical topographic device" is known as a biological optical measurement device. This device is designed to perform measurement by attaching a probe device with many probe units having a light irradiation/detection section arranged in such a way that the respective probe units sticks fast to a measurement region, for example, the head, and irradiating the region with near infrared rays from the respective probe units.

A probe device according to a conventional technology as disclosed by JP-A-2001-286449 is configured with a plurality of probe units arranged in a grid-like pattern in a shell section made of a sheet material formed into a bowl-like shape conforming to the shape of the head of an examinee. The probe units are individually detachable from the shell section and when it is confirmed from a monitor screen that the contact between a certain probe unit and the scalp is incomplete due to hair or the like, only the probe unit in question can be reattached. When attached to the head of the examinee, the probe device configured as shown above does not always fit with the head due to individual differences in the shape of the head of the examinee and differences in the region of attachment, and therefore the probe device is used with a fixing belt attached to the jaw and with the shell section firmly pressed and fixed to the head. When carrying out measurement, the prove device has such a structure that near infrared rays transmitted through each optical fiber are irradiated onto the subcutaneous region of the head through a light-emitting probe unit and reflected light is received with a light-receiving probe unit and sent back to the main unit of a measurement device through the optical fiber.

The conventional technology has a structure that projections are formed at the tips of the light-emitting probe unit and the light-receiving probe unit and the end of the optical fiber protrudes from the center of the projection. Furthermore, as another conventional example, the tip of an optical fiber is attached to a fiber holding member, an adjustment knob is provided for this fiber holding member to allow height adjustment and fine adjustment. The probe configured in this way cannot be removed from the shell section, but the tip of the optical fiber can be moved inside the shell section through the adjustment knob and when the contact between the tip of the optical fiber and scalp is not sufficient or the like, it is possible to sweep aside the hair and make an adjustment.

BRIEF SUMMARY OF THE INVENTION

According to the above described conventional technology, contact between the probe unit and the subcutaneous region of the head is realized at the tip of the light-emitting or light-receiving optical fiber arranged so as to protrude from this probe unit. In other words, contact between the probe unit and the subcutaneous region of the head constitutes "point contact." For this reason, there is a problem that it is difficult to keep the tip of the optical fiber provided so as to protrude at the tip of the probe unit arranged in the shell portion in a vertical posture with respect to the subcutaneous region of the head.

In the above described conventional example, a fine adjustment knob is provided to make the posture of the tip of the optical fiber changeable, but there is a problem that it takes time to adjust the vertical postures of many probes or the like.

Furthermore, in the above described conventional technology, since the contact between the probe and the subcutaneous region of the head is "point contact", an adjustment is made by sweeping aside the hair using the tip of this optical fiber and there is a problem that it takes time to adjust the vertical postures of many probes while sweeping aside the hair.

Therefore, it is an object of the present invention to provide a probe device provided with probe units easy to keep the vertical posture of each probe unit when attached to an examinee and easy to sweep aside the hair while keeping this vertical posture.

In order to attain the above described object, the probe device according to the present invention is used for a biological optical measurement device provided with light irradiation means for irradiating light onto the surface of a living body and light detection means for detecting intensity of light passing through the interior of the living body and emerging from the surface of the living body and includes a plurality of light irradiation probe units provided with light irradiation means at the tip, a plurality of light detection probe units provided with the light detection means at the tip, a probe support body that holds the light irradiation probe units and the light detection probe units in a mutually adjacent grid-like array and a main unit support section that supports the light detection probe units and the light irradiation probe units at predetermined positions of the probe support body, wherein the light detection probe unit is provided with a main projection formed protruding toward the surface of the living body and a plurality of sub projections arranged around the main projection, the main projection is provided with light communication means that communicates the light detection means with the outside on the axial core thereof, and the main unit support section causes the probe support body to support the sub projections in a manner pivotable around the axial core of the light communication means.

According to the present invention, it is possible to easily keep the vertical posture of each probe unit when attached to the examinee and easily sweep aside the hair while keeping this vertical posture.

Other objects, features and advantages of the invention will become apparent from the following description of the embodiments of the invention taken in conjunction with the accompanying drawings.

BRIEF DESCRIPTION OF THE SEVERAL VIEW OF THE DRAWINGS

FIGS. 17A-17D show another arrangement of a main projection and sub projections of the detection probe unit according to the fifth embodiment;

DETAILED DESCRIPTION OF THE INVENTION

Figure 6A:
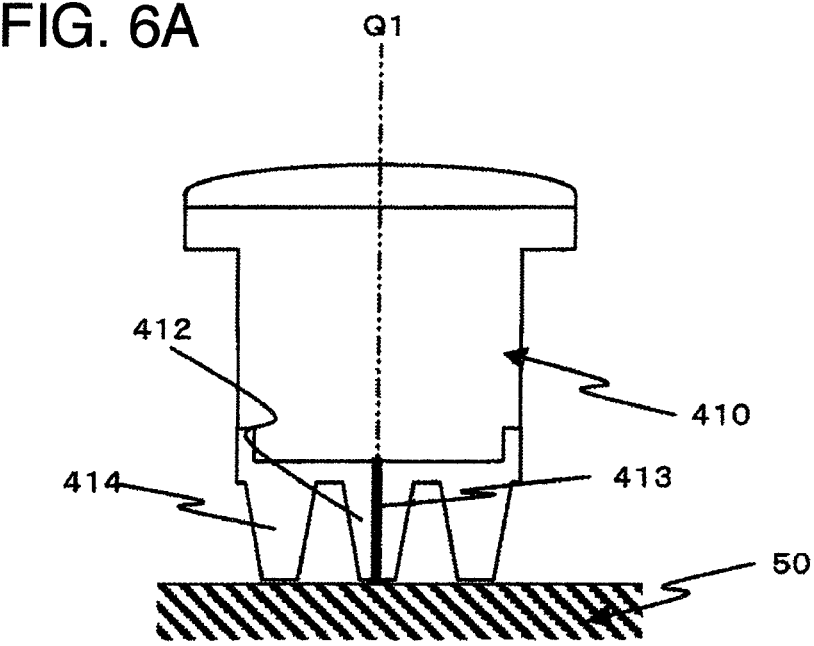
FIGS. 6A and 6B are side views showing a vertical control operation of the detection probe according to the first embodiment.
Figure 6B:
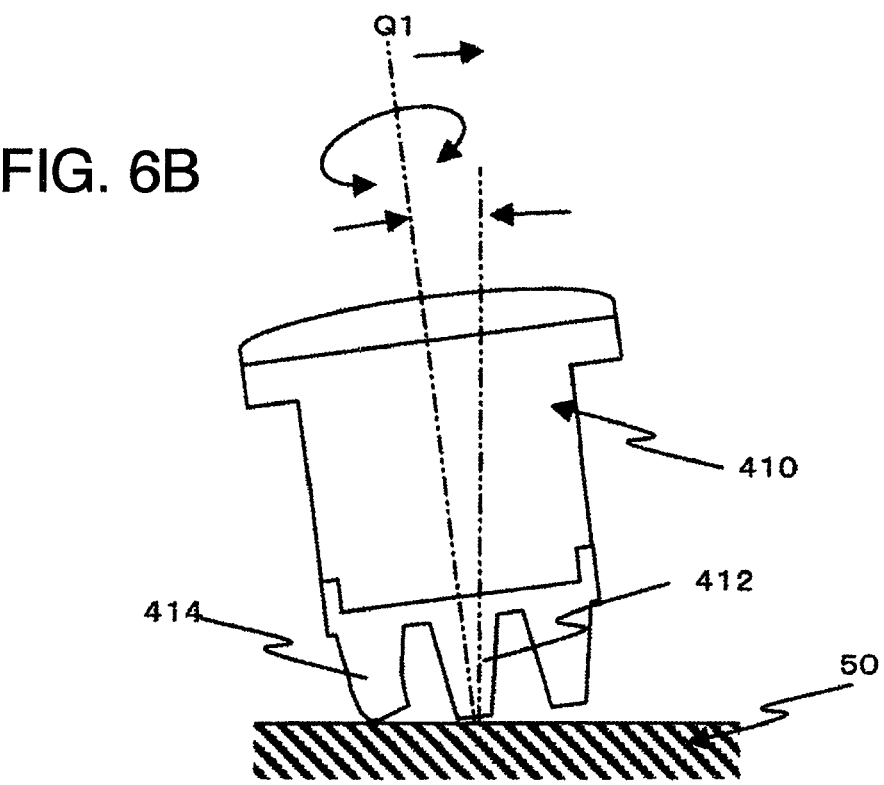
Figure 7:
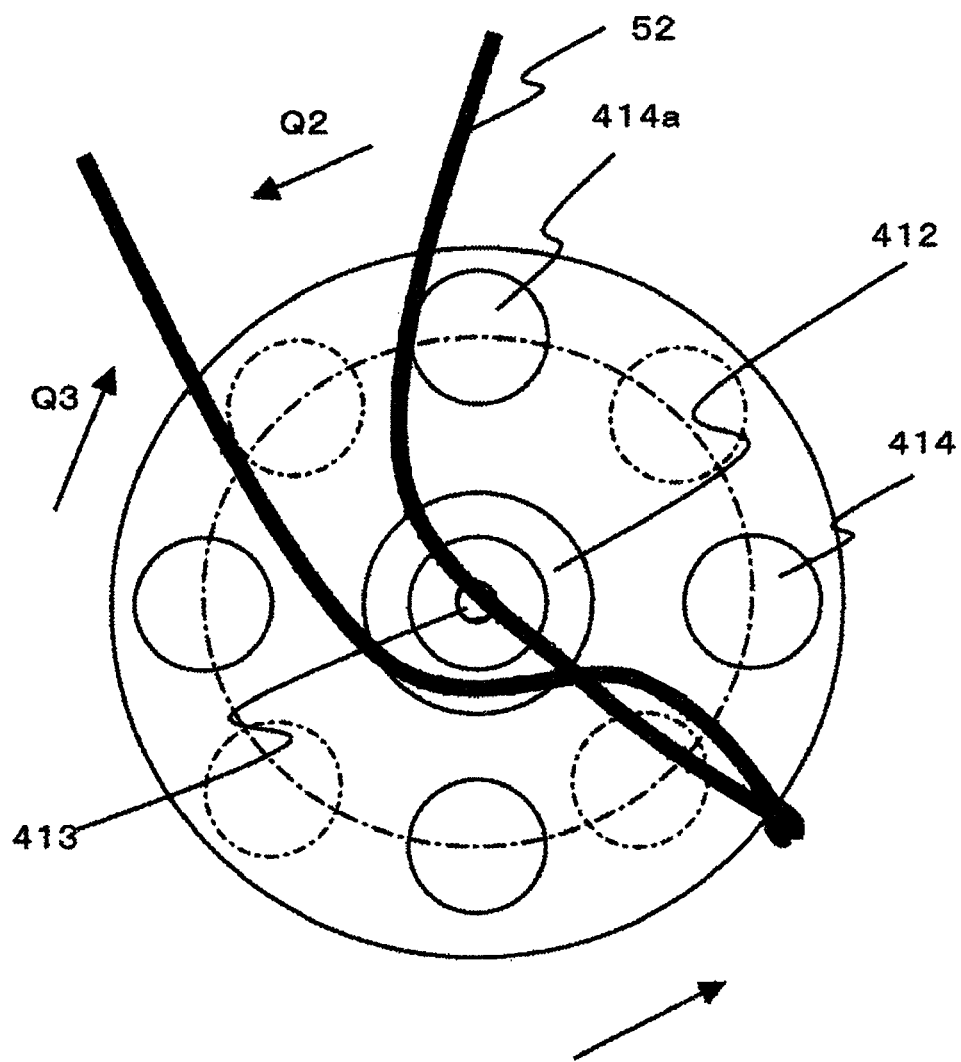
FIG. 7 is a schematic view showing a hair sweeping operation of the detection probe according to the first embodiment.
Figure 8:
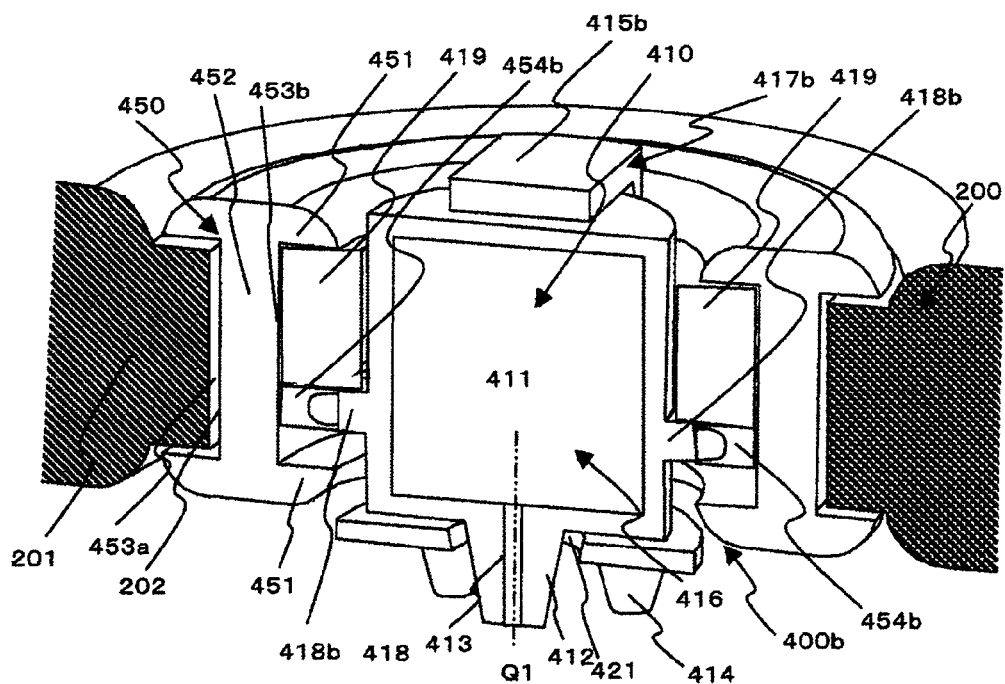
FIG. 8 is a central longitudinal cross-sectional view of a detection probe according to a second embodiment.
Figure 9:
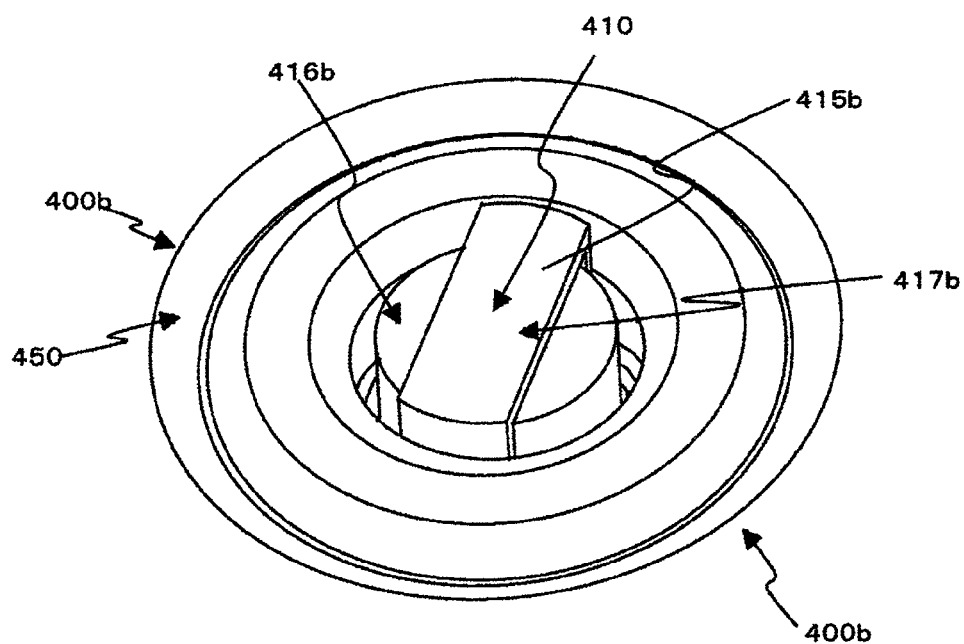
FIG. 9 is an oblique projection view of the detection probe seen from the top surface according to the second embodiment.
Figure 10:
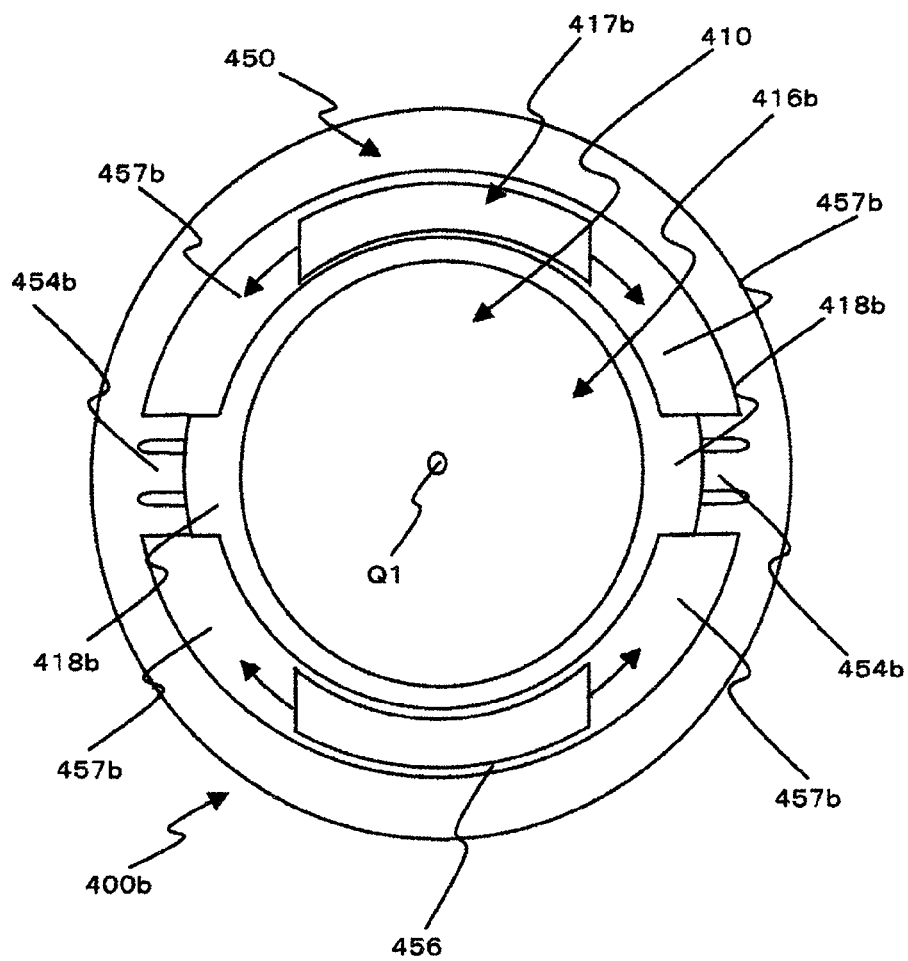
FIG. 10 is a traverse cross-sectional view of the detection probe according to the second embodiment.
Figure 11:
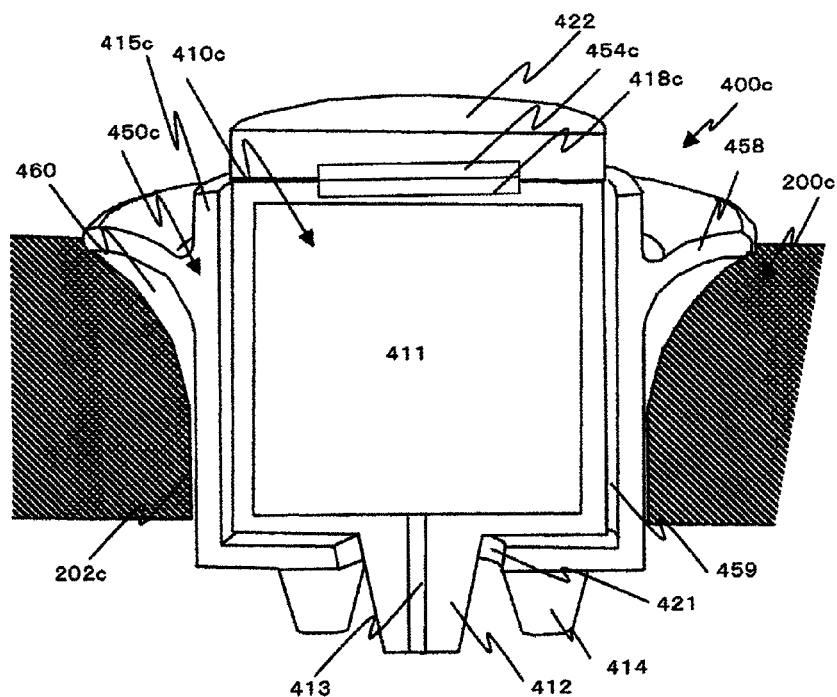
FIG. 11 is a central longitudinal cross-sectional view of a detection probe according to a third embodiment.
Figure 12:
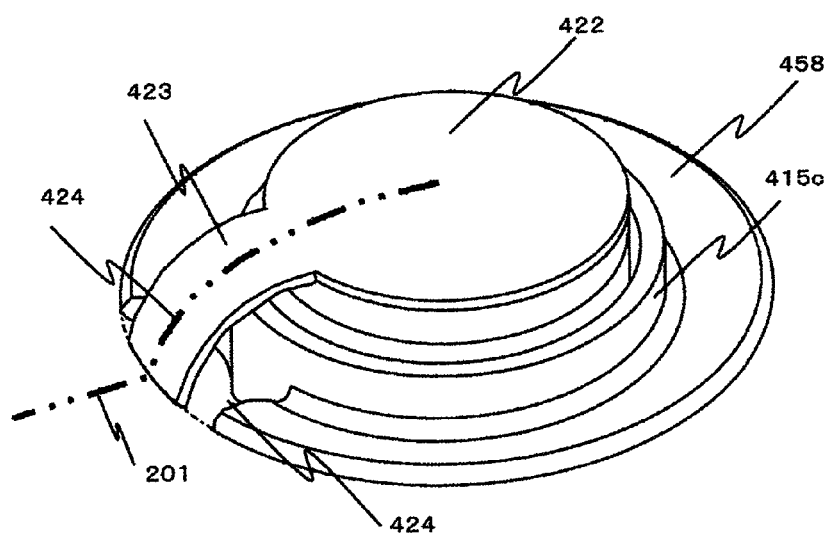
FIG. 12 is an oblique projection view of the detection probe seen from the top surface according to the third embodiment.
Figure 13:
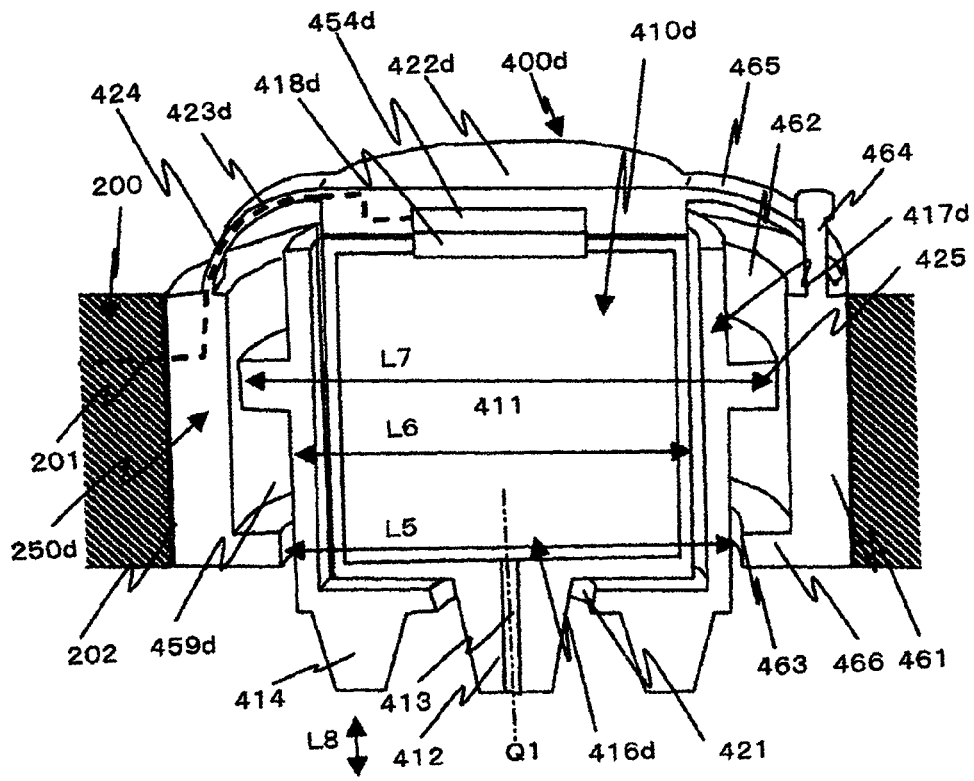
FIG. 13 is a central longitudinal cross-sectional view of a detection probe according to a fourth embodiment.
Figure 14:
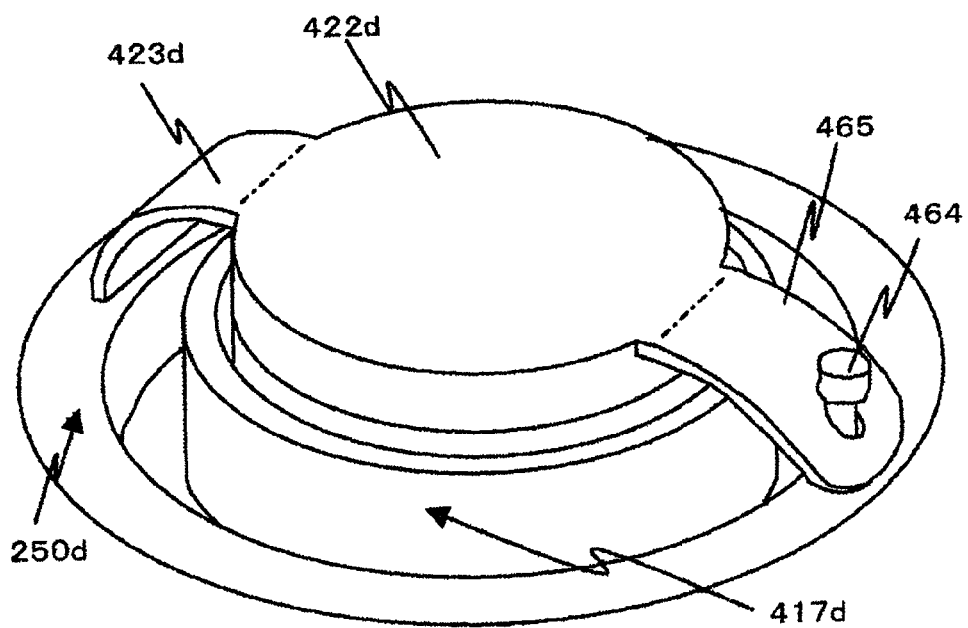
FIG. 14 is an oblique projection view of the detection probe seen from the top surface according to the fourth embodiment.
Figure 18A:
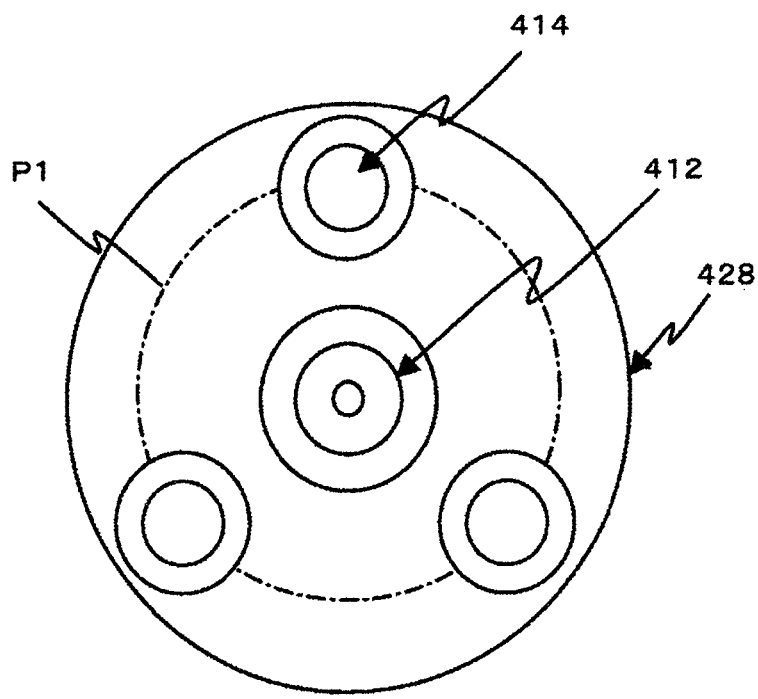
FIGS. 18A and 18B are bottom views showing the other arrangement of the sub projections according to the fifth embodiment.
Figure 18B:
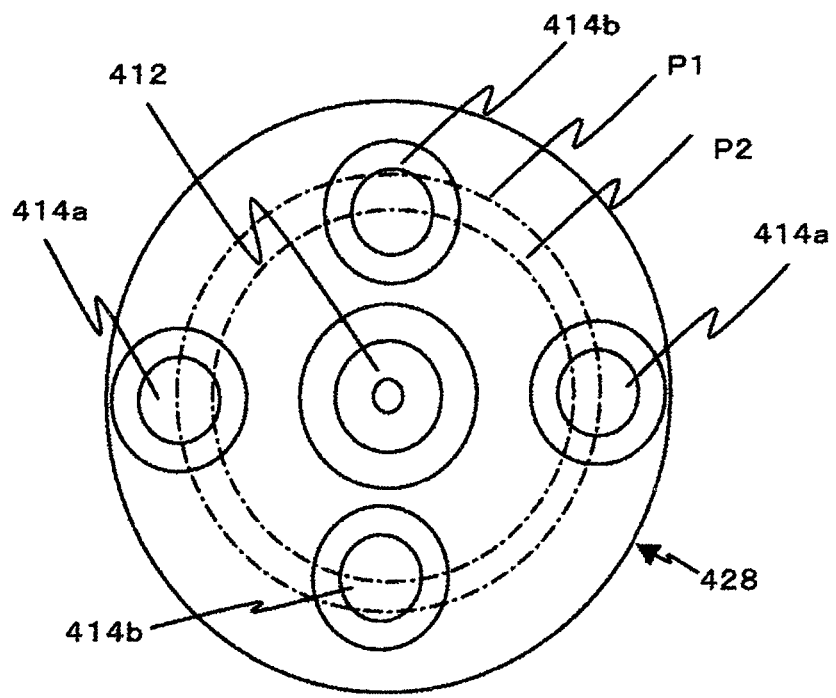
Figure 19:
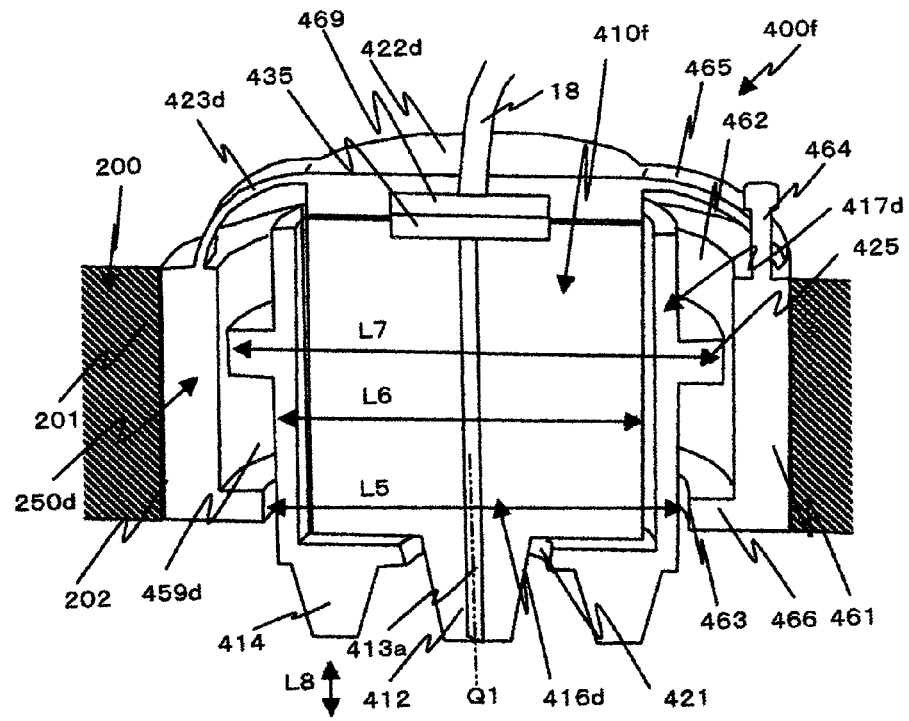
FIG. 19 is a central longitudinal cross-sectional view of a detection probe according to a sixth embodiment.
Figure 20:
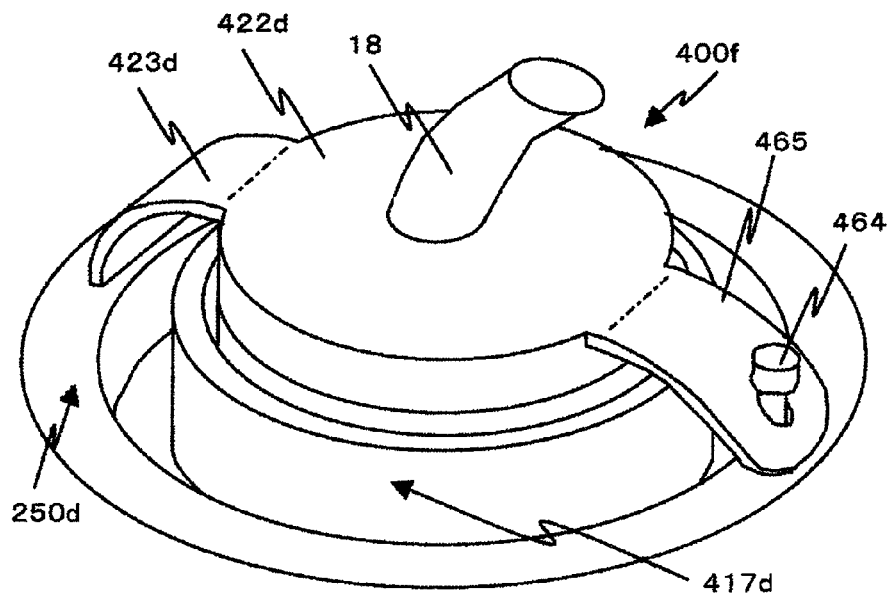
FIG. 20 is an oblique projection view of the detection probe seen from the top surface according to the sixth embodiment.

Hereinafter, a biological optical measurement device according to the present invention will be explained more specifically with reference to FIG. 1 to FIG. 20. FIG. 1 to FIG. 7 show a biological optical measurement device according to a first embodiment, FIG. 8 to FIG. 10 show a biological optical measurement device according to a second embodiment, FIG. 11 and FIG. 12 show a biological optical measurement device according to a third embodiment, FIG. 13 and FIG. 14 show a biological optical measurement device according to a fourth embodiment, FIG. 15 to FIGS. 18A and 18B show a biological optical measurement device according to a fifth embodiment, and FIG. 19 and FIG. 20 show a biological optical measurement device according to a sixth embodiment respectively. Identical parts and directions or the like are shown using identical reference numerals and overlapping explanations will be omitted.

First Embodiment

The biological optical measurement device according to a first embodiment will be explained in detail with reference to FIG. 1 to FIG. 7. The biological optical measurement device according to this embodiment is a device which measures local hemodynamic variations in a living body taking advantage of the fact that when a certain region of the brain starts to act, the amount of blood for sending oxygen to the region increases accordingly. More specifically, it is possible to simply observe the function of the brain by irradiating near infrared light from above the scalp, measuring scattering of this near infrared light by hemoglobin in the blood, thereby measuring variations in the amount of blood near the surface of the cerebrum and expressing these variations on a two-dimensional map or the like. The near infrared light here is an electromagnetic wave having an area of wavelength longer than that of visible light.

Figure 1:
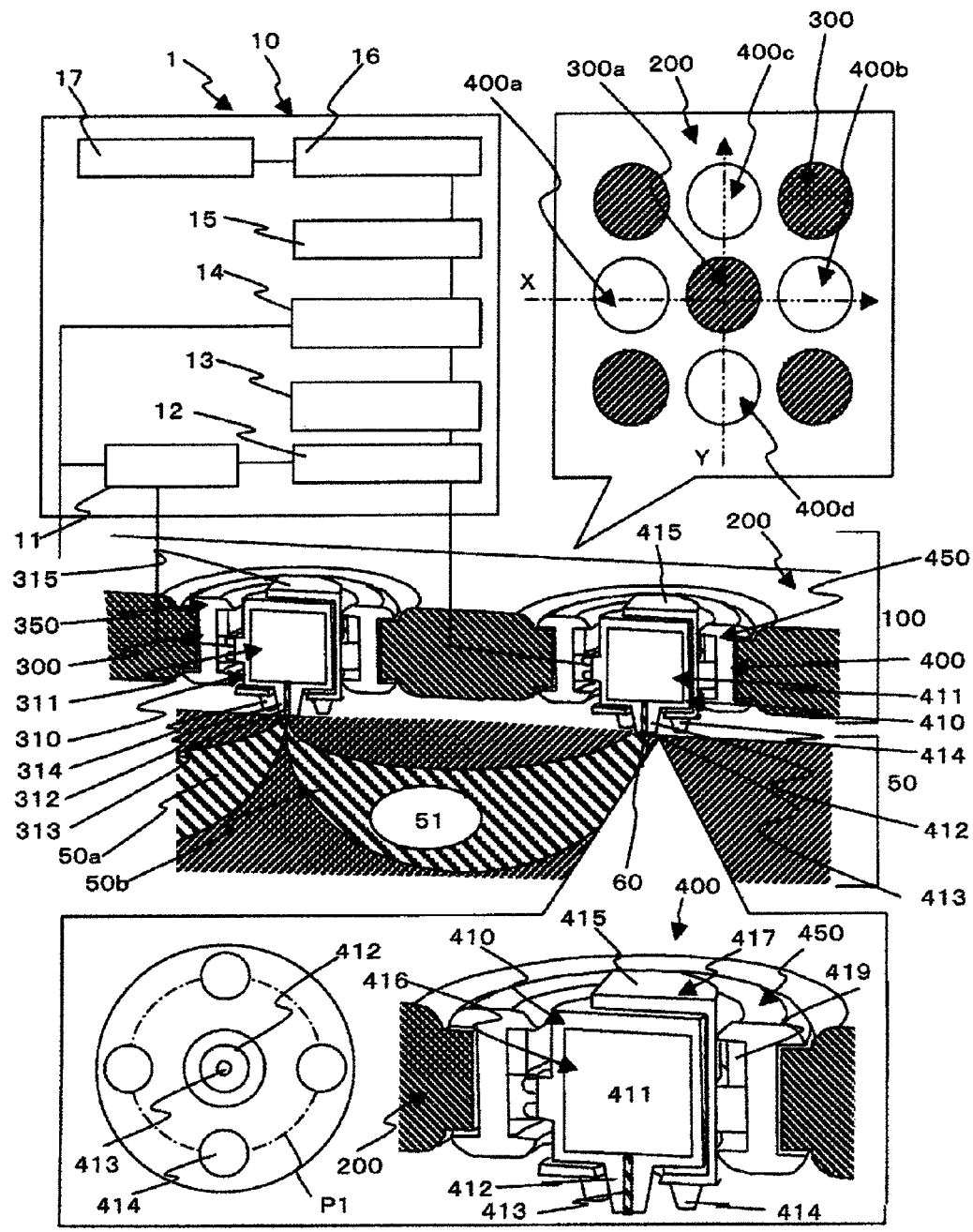
FIG. 1 is a schematic configuration diagram of a biological optical measurement device according to a first embodiment.

First, a schematic structure of the biological optical measurement device according to this first embodiment will be explained with reference to FIG. 1. FIG. 1 shows a schematic configuration of the biological optical measurement device. The biological optical measurement device generally denoted by reference numeral 1 in FIG. 1 is constructed by including a probe device 100 attached to the head of an examinee 50 and a biological optical measurement device main unit 10 which processes an image of an electric signal outputted from this probe device 100 and displays a map or the like.

The probe device 100 is composed of a probe holder 200 to be attached to the head of the examinee 50, a plurality of light-emitting probes 300 and a plurality of detection probes 400 attached to this probe holder 200 at predetermined intervals. Furthermore, the plurality of light-emitting probes 300 and detection probes 400 are arranged alternately in a matrix shape so that the detection probes 400 are arranged on both sides of the light-emitting probes 300 shown with diagonally shaded areas in a layout seen from the top surface of the probe holder 200 shown at the top right of FIG. 1.

Furthermore, the light-emitting probe 300 is constructed of a light-emitting probe unit 310 provided with a light-emitting section 311 and a light-emitting probe mounting section 350 which mounts this light-emitting probe unit 310 at the predetermined position of the probe holder 200. As the light-emitting section 311, a semiconductor laser, a titanium sapphire laser, a light-emitting diode or the like can be used, but this embodiment will explain a case with the light-emitting probe unit 310 adopting the light-emitting section 311 provided with a light-emitting diode.

Furthermore, the detection probe 400 is constructed of a detection probe unit 410 provided with a detection section 411 and a detection probe mounting section 450 which mounts this detection probe unit 410 at a predetermined position of the probe holder 200. As the detection section 411, a photoelectric conversion element such as a photodiode and photo multiplier can be used and this embodiment will explain a case with the detection probe unit 410 adopting the detection section 411 provided with a photodiode.

On the other hand, the biological optical measurement device main unit 10 is configured by including an oscillator 11 for removing noise introduced from outside, a lock amplifier 12, a logarithmic amplifier 13, a differential amplifier 14, an A/D converter 15, a calculator 16, a display section 17 and a power supply section (not shown).

According to this biological optical measurement device 1, power is supplied from the power supply section (not shown), weak near infrared light (light) of approximately 1.5 mW which is emitted from the light-emitting section 311 is condensed in a light-emitting section 311 using a lens system (not shown) and irradiated onto the head of the examinee 50 through a fiber for irradiation 313 of the main projection 312 provided in the lower part of this light-emitting section 311. The light emitted from the light-emitting section 311 is modulated in intensity by the oscillator 11 at an arbitrary frequency f of approximately 100 Hz to 10 MHz for removing noise introduced from outside.

The wavelength of the light used depends on the spectral characteristic of a target matter in the living body, but when a degree of oxygen saturation and the amount of blood are measured from the concentration of Hb and $HbO_2$ in the blood, one or a plurality of wavelengths are selected from light having a wavelength range of 600 nm to 1400 nm. The light irradiated onto the head of the examinee 50 is passed through areas of fields of view 50a, 50b of a fiber for irradiation 313, passed through an area 51 where hemodynamics locally varies such as blood vessels in this area and detected by the detection section 411 through a fiber for detection 413 of a main projection 412 formed in the lower part of the detection section 411.

As described above, since the plurality of light-emitting probes 300 and detection probes 400 are arranged alternately in a matrix form as a layout seen from the top surface of the probe holder 200 shown at the top right of FIG. 1, light irradiated from one light-emitting probe 300a can be detected by the detection section 411 of four detection probes 400a, 400b, 400c and 400d arranged on both sides in the X direction and the Y direction. In other words, one detection probe 400 can detect light irradiated from the four light-emitting probes 300 arranged on both sides in the X direction and the Y direction. That is, according to this embodiment, hemodynamic variations of the entire area to which the probe device 100 is attached can be measured.

The light detected at the detection section 411 through the fiber for detection 413 is photoelectrically converted at this detection section 411 and the intensity of the transmitting light is outputted as the intensity of an electric signal. As for the electric signal indicating the intensity of the transmitting light outputted from the plurality of detection sections 411, only the light intensity modulation frequency component of the light source is extracted by each lock-in amplifier 12, logarithmically converted by each logarithmic amplifier 13 and then inputted to the differential amplifier 14. This differential amplifier 14 inputs, for example, the output from the detection probe 400a to a negative electrode and inputs the output from the detection probe 400b to a positive electrode, and as a result, it outputs a differential signal of the intensity of the transmitting light at two different locations as an output signal. The output signal from this differential amplifier 14 is converted to a digital signal at the A/D converter 15, inputted to and processed by the calculator 16 and then displayed as time sequence data on the display device 17.

One of major features of the biological optical measurement device 1 according to this embodiment lies in that substantially the same structure is used for the light-emitting probe 300 and the detection probe 400. More specifically, though the light-emitting probe 300 and detection probe 400 differ from each other in whether the probe unit (310, 410) arranges the light-emitting section 311 or arranges the detection section 411, or whether the connection between this probe unit (310, 410) and probe mounting section (350, 450) is accompanied by supplies of power or light or acquisition of an electric signal due to this difference, other basic structures are substantially the same. Hereinafter, the detection probe 400 will be mainly explained, but if the explanation is equivalent to that of the light-emitting probe 300, the explanation of the light-emitting probe 300 will be omitted and if there is some difference, only the explanation thereof will be described.

Furthermore, another major feature of the biological optical measurement device 1 according to this embodiment is that a plurality of projections (312, 314, 412, 414) are provided for contact parts 60 of the light-emitting probe 300 and detection probe 400 with the examinee 50 and irradiation of light and acquisition of reflected light of this light are made possible through these projections.

That is, this embodiment adopts a structure in which the main projection 412 provided with the fiber for detection 413 is provided on the contact surface 60 of the detection probe unit 410 with the examinee 50 and the plurality of sub projections 414 are arranged around this main projection 412. Furthermore, this embodiment adopts a "planar structure consisting of a plurality of points" in which the light-emitting probe 300 is likewise provided with the main projection 312 provided with the fiber for irradiation 313 on the contact surface 60 with the examinee 50 and the plurality of sub projections 314 are arranged around this main projection 312.

The light-emitting probe and the detection probe of the conventional technology adopt a "one-point contact" scheme having a structure in which a fiber for irradiation or detection is directly attached to the contact surface 60 with the examinee 50 or attached reinforced with a projection. Therefore, there is a problem that it is difficult to keep the tip of the optical fiber provided so as to protrude at the tip of each of a plurality of probe units in the probe holder in a vertical posture with respect to the subcutaneous region of the head. There is a conventional technology provided with a fine adjustment knob to allow the posture of the tip of the optical fiber to be changed, yet has a problem that it takes time to adjust the vertical postures of many probes or the like.

This embodiment adopts the structure in which contact with the surface of the living body (contact surface 60) of the examinee 50 is realized by the main projections 312, 412 provided with light communication means (fiber for irradiation 313 or for detection 413) for communicating light irradiation means (light-emitting section 311) or light detection means (detection section 411) with the outside on the axial core thereof and a plurality of sub projections (314, 414) having substantially the same length and protruding around these main projections 312, 412, and can thereby easily support the light communication means in a posture perpendicular to the surface of the living body.

As illustrated in the balloon at the bottom of FIG. 1, this embodiment provides four sub projections 414 on a concentric circle P1 of the main projection 412 equidistantly, and can thereby suppress inclinations in four directions and alleviate the above described problem of the conventional technology. If there are three or more sub projections 414 around the main projection 412, the detection probe unit 410 provided with the sub projections 414 stands on its own in a vertical posture, and therefore effects similar to those described above can be expected.

This embodiment forms the sub projection 414 of a flexible resin material or a relatively soft material such as rubber or elastomer, and can thereby provide a probe device friendly to the examinee 50 and allow the detection probe unit 410 to easily keep the vertical posture. As described above, the light-emitting probe 300 can also obtain similar operations and effects by adopting the similar structure.

Furthermore, one of other major features of this embodiment is that the plurality of sub projections 414 are supported in a manner pivotable around the main projection 412.

This type of the biological optical measurement device has a problem that the hair on the surface of the living body interferes making it difficult to cause the tip of the optical fiber to stick fast to the surface of the living body of the examinee 50. However, according to the conventional technology, the contact between the probe and the subcutaneous region of the head is a "one-point contact" and the tip of this optical fiber makes an adjustment by sweeping aside the hair, and therefore there is a problem that it takes time to adjust the vertical postures of many probes while sweeping aside the hair.

In this embodiment, the sub projections 414 are supported in a manner pivotable around the main projection 412, and therefore by rotating these sub projections 414, the tips of the sub projections 414 sweep aside the hair allowing the tip of the fiber for detection 413 to easily stick fast to the surface of the living body. Moreover, when the sub projections 414 rotate around the main projection 412, it is possible to cause the detection probe unit 410 to easily take the vertical posture. Moreover, by forming the sub projections 414 of a flexible material and providing the fiber for detection 413 on the axial core and making the flexible sub projections 414 rotate around the main projection 412 having a higher degree of strength than the sub projections 414, it is possible to easily perform hair sweeping and posture control.

As described above, by adopting a similar structure, the light-emitting probe 300 can have similar operations and effects.

Furthermore, one of other major features of this embodiment is that the support body 415 of the sub projections 414 is exposed from the outside surface of the probe holder 200 and this support body 415 is pivotably attached to the detection probe mounting section 450. In this way, even after the probe device 100 is attached to the examinee, it is possible to pick up and turn the support body 415 exposed from the outside surface of the probe holder 200 by fingers or the like and thereby simply rotate the sub projections 414.

As described above, since the light-emitting probe 300 also has a similar structure, providing a support body 315 allows similar operations and effects to be obtained.

Furthermore, one of other major features of this embodiment lies in that the detection probe unit 410 is configured by including a first housing 416 provided with the detection section 411 and the main projection 412 and a second housing 417 provided with the sub projections 414 and the support body 415, the first housing 416 is fixed to and supported by the detection probe mounting section 450 and the second housing 417 is pivotably attached to the detection probe mounting section 450 or the first housing 416.

According to the embodiment having this feature, since only the sub projections 414 can be turned while leaving the main projection 412 in contact with the surface of the living body as is, it is possible to make easier the connection between the first housing 416 provided with the detection section 411 and an external device or the electrical connection through the detection probe mounting section 450. Especially, in this embodiment, since the detection probe 400 and the first housing 416 are connected through a connection section 418, it is possible to connect an electric signal outputted at the detection section 411 to a signal wiring in the probe holder 200 through the connection section 418, and on the other hand, by rotating the second housing 417 and thereby rotating the sub projections 414 without influencing electrical connections, it is possible to move the hair and further keep the first housing 416 in a vertical posture.

The light-emitting probe 300 is also provided with a first housing and a second housing having similar structures, making easier the connection between the first housing provided with the light-emitting section 311 and an external device or power supply to the light-emitting section 311 through the light-emitting probe mounting section.

Furthermore, one of other major features of this embodiment is that a cushion material section 419 is provided around the detection probe unit 410 and the detection probe unit 410 is attached to the detection probe mounting section 450 through this cushion material section 419. According to this structure, it is possible to improve the degree of contact of planar contact made up of a plurality of point contacts in accordance with the unevenness of the surface of the living body of the examinee 50.

Furthermore, one of other major features of this embodiment is that the detection probe unit 410 is attached to the detection probe mounting section in a detachable manner. This makes it possible to replace the detection probe unit 410.

Furthermore, one of other major features of this embodiment is that the second housing 417 provided with the sub projections 414 is provided in a detachable manner. This makes it possible to replace parts of the sub projections 414 which contact the examinee 50.

Figure 2:
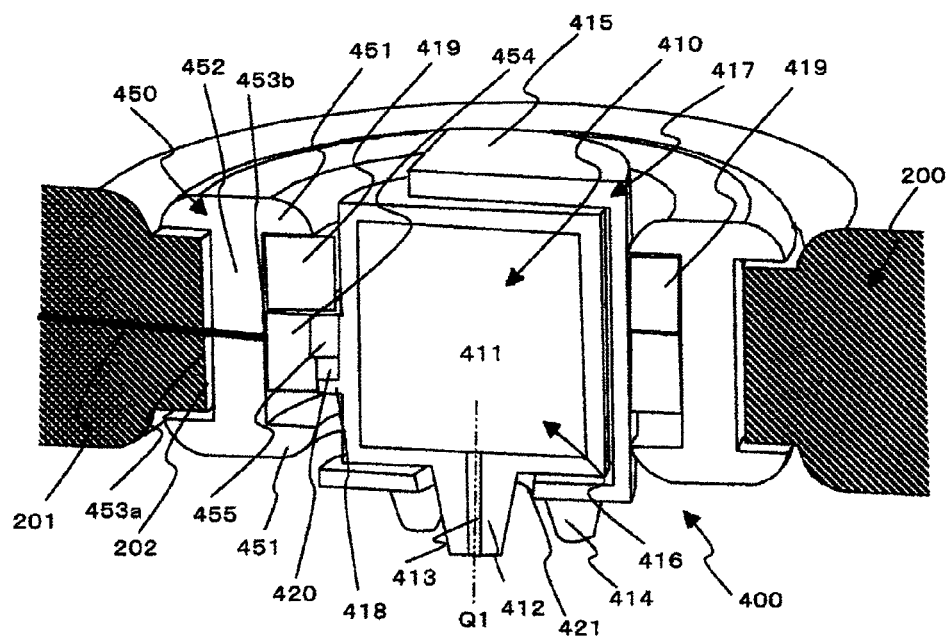
FIG. 2 is a central longitudinal cross-sectional view of a detection probe according to the first embodiment.
Figure 3:
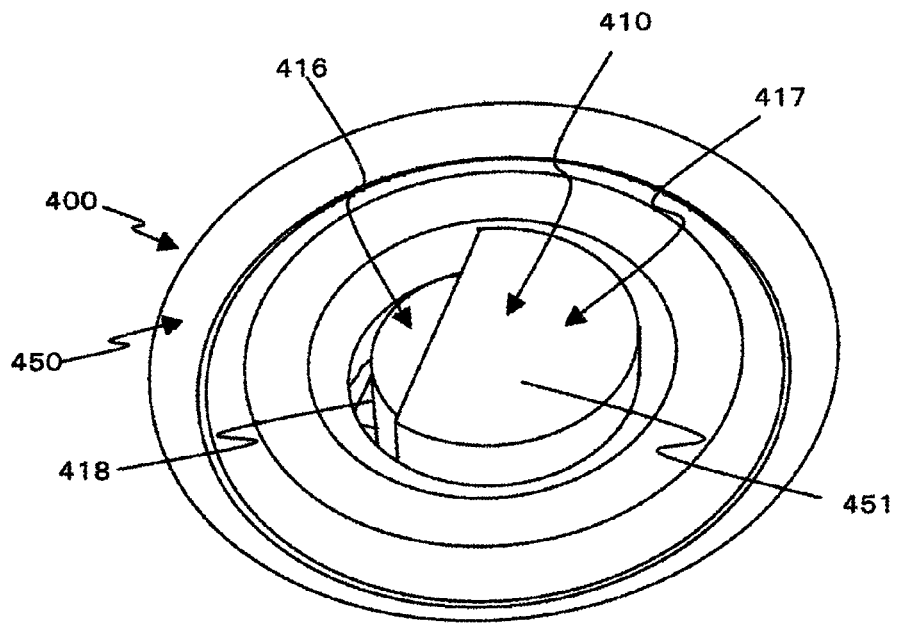
FIG. 3 is a perspective view of the detection probe seen from the top surface according to the first embodiment.
Figure 4:
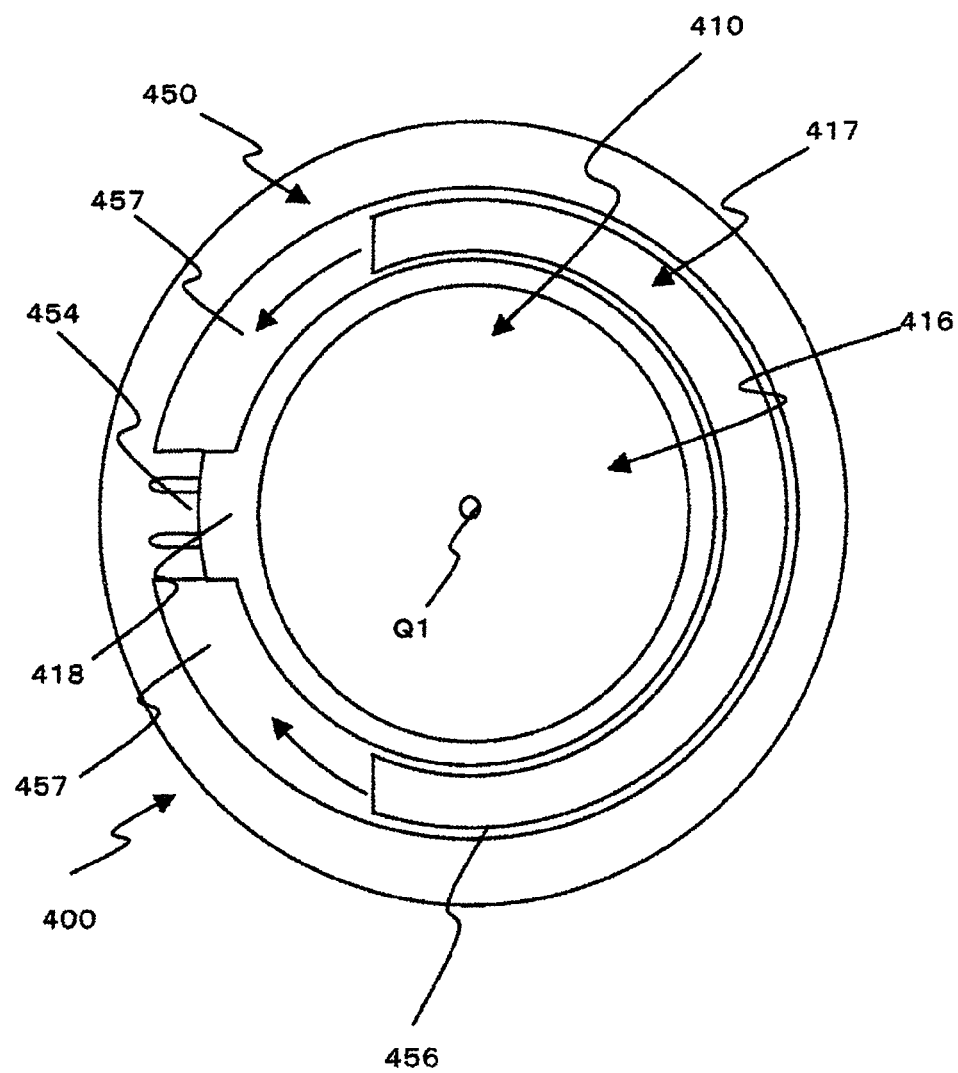
FIG. 4 is a traverse cross-sectional view of the detection probe according to the first embodiment.
Figure 5A:
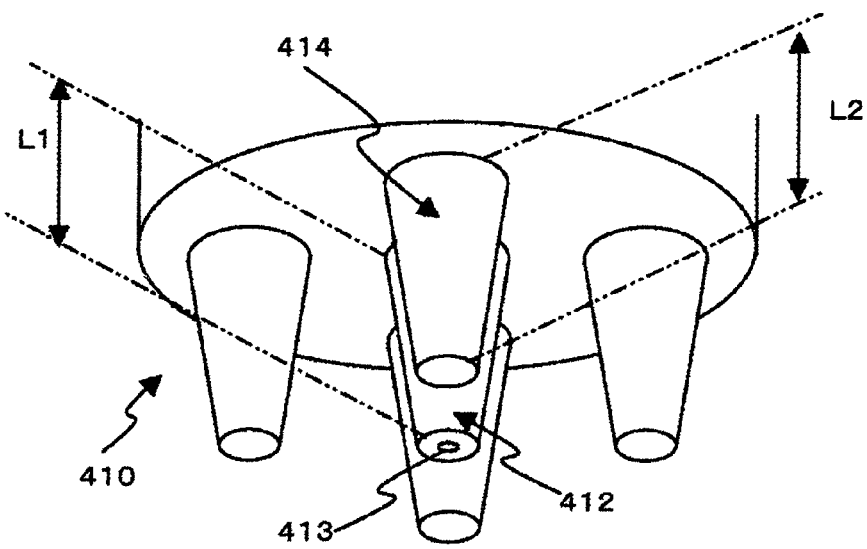
FIG. 5A is an oblique projection view showing the projections according to the first embodiment.
Figure 5B:
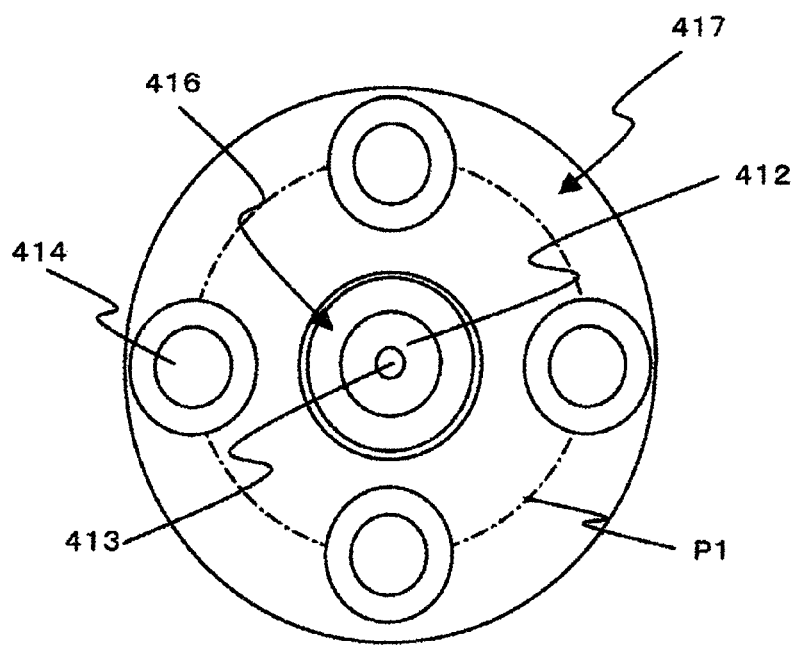
FIG. 5B is a front view showing an arrangement of the projections.

Hereinafter, the probe device 100 which constitutes a major feature of the biological optical measurement device 1 according to this embodiment will be explained more specifically with reference to FIG. 2 to FIG. 7. As described above, the detection probe 400 will be explained more specifically in the following explanations, but since the light-emitting probe 300 also has a similar structure and similar operations and effects, specific explanations thereof will be omitted. Here, FIG. 2 is a central longitudinal cross-sectional view of the detection probe. FIG. 3 is a perspective view of the detection probe seen from the top surface. FIG. 4 is a traverse cross-sectional view of the detection probe. FIGS. 5A and 5B show the projections, FIG. 5A is a partial perspective view of the detection probe unit and FIG. 5B is a bottom view of the detection probe unit. FIGS. 6A and 6B show a vertical control operation of the detection probe, FIG. 6A is a side view of the detection probe in a vertical posture and FIG. 6B is a diagram illustrating the posture control operation. FIG. 7 is a diagram illustrating a hair sweeping operation.

First, in FIG. 2, a wiring to be led to the biological optical measurement device main unit 10 is provided inside the probe holder 200 for attaching the detection probe 400 at a predetermined position and a signal line 201 is wired. This wire is bundled at an end of the probe holder 200 and connected to the biological optical measurement device main unit 10. In the same way, a power cable (not shown) is also provided in this probe holder 200 to supply power to the light-emitting probe 300 and this power cable is also bundled at a predetermined position and connected to the biological optical measurement device main unit 10 as in the case of the signal line 201.

Furthermore, as explained in FIG. 1, an opening 202 is formed in the probe holder 200 to attach the light-emitting probes 300 and detection probes 400 at matrix-shaped intersections and the light-emitting probe mounting section 350 or detection probe mounting section 450 is alternately attached to this opening 202 and the signal line 201 or power cable is connected to each section. FIG. 2 shows a cross-sectional view of the detection probe 400 attached to the opening 202.

In this embodiment, the diameter of the light-emitting probe mounting section 350 or the detection probe mounting section 450 is assumed to be approximately 20 mm and the interval of the matrix-shaped intersections is set to 30 mm. A distance between the fiber for irradiation 313 and the fiber for detection 413 adjacent to each other is set to 30 mm. Furthermore, the thickness of probe holder 200 is set to 15 mm. Incidentally, in the probe device 100 for children, the distance between the fiber for irradiation 313 and the fiber for detection 413 adjacent to each other may be set to 20-30 mm.

The detection probe mounting section 450 is configured by including a ring-shaped base 452 having an "I-shaped" cross-section provided with an overhang 451 which protrudes to the inner and outer perimeters in an edged shape at the top and bottom ends, a connection receiving section 454 attached inside this ring-shaped base 452 and a cushion material section 419. A recessed part 453a is formed between the upper and lower overhangs 451 on the perimeter of the ring-shaped base 452 and the end of the opening 202 engages with this recessed part 453a.

Here, the thickness of the recessed part 453a is smaller than the thickness of the probe holder 200 and when the opening 202 is fitted into this recessed part 453a, the surface and the back of the opening 202 are caved in and set to a size that the overhangs 451 can be fitted into this cave-in part. In this way, the upper and lower surfaces of the detection probe mounting section 450 are made flush with the surface of the probe holder 200 and it is thereby possible to adopt a structure in which the detection probe 400 conforms to the probe holder 200.

Also, the connection receiving section 454 coupled with the connection section 418 is provided at a predetermined position of the internal circumference of a recessed part 453b inside the ring-shaped base 452. This connection receiving section 454 couples with the connection section 418 and thereby supports the detection probe unit 410 like a cantilever and is also electrically connected therewith. In this embodiment, the connection receiving section 454 is provided with a protruding lug 455 and the connection section 418 is provided with a groove 420 which engages with this lug 455. The engagement between the lug 455 and the groove 420 is realized by inserting the detection probe unit 410 from below the detection probe mounting section 450, sliding the lug 455 and inserting into the groove 420 from below. The strength of this engagement is set to a level enough to keep and connect the detection probe unit 410 dynamically as well as electrically.

The cushion material section 419 has a ring shape arranged along the overhang 451 in the upper part of the recessed part 453b inside. This cushion material section 419 is provided with the function to prevent the connection section 418 from moving upward. That is, the cushion material section 419 becomes an appropriate buffering material between the detection probe mounting section 450 and the detection probe unit 410 and absorbs stress which the detection probe unit 410 receives from the examinee side, and can thereby cause the tip of the main projection 412 provided at the tip of the detection probe unit 410 to stick fast to the surface of the living body of the examinee 50 conforming to the unevenness thereof. Furthermore, the inclination of the detection probe unit 410 caused by the unevenness of the surface of the living body of the examinee 50 can also be absorbed by providing this cushion material section 419.

Furthermore, in this embodiment, since the detection probe unit 410 can be freely attached/detached to/from the probe holder 200, it is possible to replace the detection probe unit 410 and improve cleanability.

The detection probe unit 410 is constructed of the first housing 416 provided with the detection section 411, main projection 412 and fiber for detection 413 and second housing 417 that covers the perimeter of the first housing 416. The first housing 416 basically has a columnar shape and has an appearance provided with the main projection 412 which protrudes like a circular truncated cone in the center of this column-shaped bottom surface. The detection section 411 is provided inside this column, a linear fiber for detection 413 to transmit light to the detection section 411 is provided on the central axis Q1 of the main projection 412 and the connection section 418 is provided at a predetermined position of the circumferential surface of the column.

In this embodiment, the first housing of the light-emitting probe unit 310 also has a structure substantially equivalent to that of the first housing 416 of this detection probe unit 410 and differs in the light-emitting section 311 instead of the detection section 411 and in that power is supplied from the connection section 418. This embodiment has explained that the detection section 411 is a photo diode, but it is also possible to reduce the sizes of the lock amplifier 12 and logarithmic amplifier 13 or the like and fit them into the area of this detection section 411 compactly. It has been likewise explained that the light-emitting section 311 is a light-emitting diode, but it is also possible to reduce the size of the oscillator 11 or the like and provide it in the area of this light-emitting section 311.

The second housing 417 has an outside shape that covers part of the top surface, bottom surface and circumferential surface of the first housing 416. That is, the bottom surface of the second housing 417 has the size that covers the whole bottom surface of the first housing 416, provides an opening hole 421 which exposes the main projection 412 provided in the first housing 416 in the center and the sub projections 414 are provided around this opening hole 421. On the other hand, the perimeter and top surface of the second housing 417 are formed into a cylindrical shape, part of which is cut out so as to expose the circumferential surface to which the connection section 418 is attached. The top surface of the second housing 417, part of which is cut out constitutes the support body 415 formed so as to protrude upward from the top surface of the detection probe mounting section 450.

FIG. 3 shows an appearance perspective view of the detection probe 400 when the support body 415 which protrudes outward is seen from above. According to the structure of this detection probe 400, by rotating the support body 415 which protrudes in a semicircular shape in the center of the detection probe 400 and thereby rotating the plurality of sub projections 414 provided in the lower part of this support body 415, it is possible to move the hair from right below the main projection 412. Furthermore, adopting a semicircular shape for the support body 415 makes it easier to pick it up by fingers or the like and allows the rotation condition to be visually checked.

Furthermore, FIG. 4 shows a traverse cross-sectional view of the detection probe 400 to explain the rotation range of the second housing 417 provided with the support body 415. As is clear from FIG. 4, the second housing 417 covers the circumferential surface of the first housing 416 so as to partially expose the circumferential surface of the first housing 416 to which the connection section 418 is attached. For this reason, a space 457 where the second housing 417 having a half-ring shaped cross-section can rotate is formed on both sides of the joint between the connection section 418 and connection receiving section 454. This allows the second housing 417 to rotate around the center axis Q1 in the space between the detection probe mounting section 450 including this space 457 and the first housing 416 as a moving path 456.

Next, the structure, operations and effects of the main projection 412 and sub projections 414 will be further explained with reference to FIGS. 5A and 5B to FIG. 7. In FIGS. 5A and 5B, this embodiment provides the main projection 412 and sub projections 414 having substantially the same heights L1, L2 on the bottom surface (the surface on the examinee 50 side) of the detection probe unit 410. Furthermore, providing the main projection 412 and sub projections 414 in a circular truncated cone shape which is thick at the root and becomes thinner toward the tip improves the flexibility when contacting the scalp of the examinee 50 and processability during molding. This embodiment improves the closeness of contact with the scalp of the examinee 50 by forming the second housing 417 provided with sub projections 414 of a flexible resin material or a relatively soft material such as rubber and elastomer.

In this embodiment, the heights of the main projection 412 and sub projections 414 are set to within a range of 3 mm to 5 mm and the diameter of the bottom surface of the second housing 417 to which the main projection 412 and sub projection 414 are attached is set to 17 mm.

Furthermore, this embodiment also forms the first housing 416 of a flexible resin material or a relatively soft material such as rubber and elastomer. Therefore, the main projection 412 provided for this first housing 416 is also formed of a relatively soft material. As explained in FIG. 4, in this embodiment, part of the circumferential surface of the second housing 417 is cut out so as to allow the second housing 417 to rotate around the first housing 416 while seguring the coupling between the connection receiving section 454 and connection section 418.

Using this partially cut-out shape, this embodiment allows the first housing 416 to be separated from the second housing 417. In other words, the detection probe 400 can be removed from the detection probe mounting section 450 and further the second housing 417 can be separated. This allows the second housing 417 provided with the sub projections 414 which move on the scalp of the examinee 50 to be replaced, which is therefore hygienic. Especially, this embodiment can replace only the sub projections 414 which move except the main projection 412 which is provided with the fiber for detection 413 inside and hard to be replaced and can thereby reduce the cost.

Furthermore, as shown in FIG. 5B, the four sub projections 414 are provided equidistantly on the concentric circle P1 of the main projection 412 and in this way as shown in FIG. 6A, the detection probe unit 410 can stand on its own on the scalp of the examinee 50 in a vertical posture. This makes it possible to keep the fiber for detection 413 provided on the central axis Q1 of the main projection 412 in a vertical posture and thereby improve the accuracy.

Furthermore, when the probe device 100 is attached to the examinee 50 as shown in FIG. 6B, if the central axis Q1 of the detection probe unit 410 is in an inclined posture, it is possible to pick up the support body 415 to rotate the second housing 417, thereby bring the central axis Q1 of the detection probe unit 410 closer to the vertical position and put it in a vertical posture as shown in FIG. 6A. In this case, using the cushion material section 419 together makes the above described posture control operation easier. Furthermore, as shown in FIG. 6B, forming the sub projection 414 of a flexible material can improve the posture control operation using this elasticity. Especially, the main projection 412 is provided with the fiber for detection 413 on the axial core and it is harder compared with the flexible sub projections 414, and it is thereby possible to improve the posture control operation accompanying the rotation.

Furthermore, as shown in FIG. 7, this embodiment has operations and effects of sweeping aside the hair of the scalp of the examinee 50 accompanying the rotation of the sub projections 414. FIG. 7 shows a situation in which when the probe device 100 is attached, the hair is located right below the main projection 412 interfering detection from the fiber for detection 413. In such a situation, since this embodiment can rotate the sub projections 414 around the fiber for detection 413, the rotation and movement of the tips of the sub projections 414 can move this interfering hair. For example, in FIG. 7, since the interfering hair 52 is blocking the fiber for detection 413 with a certain length, this hair 52 is located in a posture across a plurality of sub projections 414. When the sub projections 414 rotate in the Q2 direction in this condition, the sub projection 414a moves the crossing hair 52, and can thereby move the hair 52 which is blocking the fiber for detection 413. As for the rotation operation of the sub projections 414, rotating them in the Q2 direction and Q3 direction which is opposite thereto alternately can even move the flexible hair 52. This embodiment sets the range in which the sub projections 414 rotate to between 30 to 90 degrees.

Second Embodiment

Next, a detection probe 400b according to a second embodiment will be explained in detail with reference to FIG. 8 to FIG. 10. Parts common to those in the first embodiment are assigned the same reference numerals and overlapping explanations will be omitted. Furthermore, since the light-emitting probe also has a structure similar to that of this detection probe 400b, explanations thereof will be omitted. Here, FIG. 8 is a central longitudinal cross-sectional view of the detection probe. FIG. 9 is a perspective view of the detection probe seen from the top surface. FIG. 10 is a traverse cross-sectional view of the detection probe.

In FIG. 8, one feature of the detection probe 400b according to this second embodiment lies in that a first housing 416b is supported on both sides with respect to a detection probe mounting section 450. The first embodiment adopts the cantilever supporting structure whereby the connection section 418 is provided on one circumferential surface of the first housing 416 having a cylindrical appearance and this connection section 418 is supported by the connection receiving section 454, whereas this second embodiment adopts a both-side supporting structure in which connection sections 418b are provided on circumferential surfaces on both sides of the first housing 416b having a cylindrical appearance and these connection sections 418b are supported by connection receiving sections 454b on both sides. According to this embodiment, since the first housing 416b can be supported on both sides, the first housing 416b can be supported more reliably.

Furthermore, since the connection between the connection section 418b and the connection receiving section 454b can be distributed on both sides, the sizes of the individual connection sections 418b and connection receiving sections 454b can be reduced. Furthermore, since electric connections can also be distributed between the connection sections 418b and connection receiving sections 454b on both sides, downsizing can be realized in this aspect, too. Electric connections can be concentrated on one coupling section to thereby simplify the wiring of a probe holder 200. Furthermore, since the coupling structure between the connection sections 418b and connection receiving sections 454b is similar to that of the first embodiment, detailed explanations thereof will be omitted.

Furthermore, another feature of the detection probe 400b according to this second embodiment lies in that the appearance structure of the second housing 417b has been changed by adopting a both-side supporting structure. That is, the second housing 417 of the first embodiment has adopted the structure in which one side of the cylindrical shape is cut out to avoid the coupling of a set of the connection section 418 and connection receiving section 454, whereas this second housing 417b adopts a structure in which both sides of the cylindrical shape are cut out to avoid the coupling of two sets of the connection section 418b and connection receiving section 454b.

That is, as for this second housing 417b according to this embodiment, strip-shaped support bodies 415b are formed which extend upward from both sides of the bottom surface of the circle provided with sub projections 414 and coupled together at the top of the first housing 416b. FIG. 9 shows an appearance perspective view of the detection probe 400b when this strip-shaped support body 415b is seen from above.

According to the structure of this detection probe 400b, by rotating the support body 415b which protrudes in a strip shape in the center of the detection probe 400b and thereby rotating a plurality of sub projections 414 provided in the lower part of this support body 415, it is possible to move the hair 52 from right below the main projection 412. Furthermore, in this case, adopting the strip-shaped support body 415b makes it easy to pick it up by fingers or the like and makes it possible to visually check the rotation situation.

Furthermore, FIG. 10 shows a traverse cross-sectional view of the detection probe 400b to illustrate the rotation range of a second housing 417b provided with the support body 415b. As is clear from FIG. 10, the second housing 417b is formed in spaces other than those of the connection section 418b and connection receiving section 454b provided on both sides of the first housing 416b so as to avoid these sections. For this reason, spaces 457b in which the second housing 417b can rotate are formed on both sides of the joint between the respective connection sections 418b and connection receiving sections 454b. This allows the second housing 417b to rotate around the central axis Q1 using the space between the detection probe mounting section 450 including this space 457b and the first housing 416b as a moving path 456.

Third Embodiment

Next, a detection probe 400c according to a third embodiment will be explained in detail with reference to FIG. 11 and FIG. 12. Parts common to the first and second embodiments are assigned the same reference numerals and overlapping explanations will be omitted. The light-emitting probe also has a structure similar to that of this detection probe 400c, and therefore explanations thereof will be omitted. Here, FIG. 11 is a central longitudinal cross-sectional view of the detection probe. FIG. 12 is a perspective view of the detection probe seen from the top surface.

In FIG. 11, one of features of the detection probe 400c according to this third embodiment lies in that a probe holder 200c is formed of rubber or a flexible resin material, an opening 202c which is formed at a predetermined position of this probe holder 200c is formed with certain hardness and the detection probe 400c is fitted into this opening 202c in a detachable and pivotable manner.

This embodiment adopts a structure in which the perimeter of the detection probe 400c is formed of rubber or a flexible resin material, this detection probe 400c formed of rubber or a flexible resin material is inserted into the opening 202c formed of a similar material and the detection probe 400c is held to the probe holder 200c in a detachable and pivotable manner through friction between both members accompanying this insertion.

A cap 422 connected to the top of the detection probe 400c is attached to the opening 202c of the probe holder 200c via a coupling member 423. This cap 422 is provided with a connection receiving section 454c and this connection receiving section 454c is connected to a signal line 201 of a probe holder 200 through the signal line 424 provided for a coupling member 423.

On the other hand, the detection probe 400c is constructed of a detection probe mounting section 450c inserted into the opening 202c and a detection probe unit 410c which is inserted into this detection probe mounting section 450c.

The detection probe mounting section 450c has a cylindrical shape whose upper part is open and a mounting flange 458 protruding therearound is formed in the upper part of the circumferential surface thereof, and an opening which exposes a main projection 412 and a plurality of sub projections 414 formed around this opening 421 are formed in the bottom surface.

The mounting flange 458 has a petal-like shape which extends diagonally upward. By leaving a cylindrical circumferential part 415c in a size that can be picked up by fingers above the mounting flange 458, it is possible to attach/detach and rotate this detection probe 400c. Furthermore, by providing a notch 424 in the vicinity of the coupling member 423 as shown in FIG. 12, this mounting flange 458 can rotate the detection probe 400c.

Furthermore, the detection probe unit 410c has a columnar appearance that can be inserted into a main unit storage section 459 formed inside the detection probe mounting section 450c, a main projection 412 is provided in the center of the bottom surface of this columnar shape and a connection section 418c to be connected to the connection receiving section 454c is provided on the top surface. Here, as for the engagement between main unit storage section 459 and the detection probe unit 410c, the inner diameter and the outside shape are set so as to have strength enough to keep a positional relationship between both members by means of friction between the contact surfaces of both members or the like.

According to this embodiment, the detection probe unit 410c is inserted up to a position at which the main projection 412 of this detection probe unit 410c protrudes from the opening 421 of the detection probe mounting section 450c through the opening formed in the upper part of the detection probe mounting section 450c first, and it is thereby possible to couple this detection probe unit 410c with the detection probe mounting section 450c to assemble the detection probe unit 400c. This detection probe 400c is inserted into the opening 202c of the probe holder 200c and the connection receiving section 454c of the cap 422 is coupled with the connection section 418c, and it is thereby possible to attach the detection probe 400c to the probe holder 200c electrically as well as structurally.

In this way, according to the detection probe 400c mounted in the probe holder 200c, when the probe device 100 is attached to the examinee 50, the contact between the scalp of the examinee 50 and the tip of the main projection 412 can be adjusted with the engagement between the detection probe 400c and the opening 202c. Especially, this embodiment adopts the mounting flange 458 having a petal-shape which is open to the outside in an inward curve and thereby provides a height difference adjusting space 460 in a gap with the opening 202c, and therefore it is possible to adjust the depth of insertion of the detection probe 400c with respect to the opening 202c using this height difference adjusting space 460 and thereby satisfactorily keep contact between the scalp of the examinee 50 and the tip of the main projection 312.

Furthermore, when contacting the scalp of the examinee 50 with the tip of the main projection 412, it is possible to adjust the height (insertion width) of the main projection 412 and adjust the height difference (insertion width) of the sub projections 414 separately and thereby improve the closeness of contact.

Furthermore, the sub projections 414 can be rotated around the central axis Q1 by picking up the circumferential part 415c provided above the mounting flange 458 by fingers. In this case, the rotation of the detection probe unit 410c is restrained because of the connection of the cap 422 and it is thereby possible to rotate only the sub projections 414 a great deal.

Fourth Embodiment

Next, a detection probe 400d according to a fourth embodiment will be explained with reference to FIG. 13 and FIG. 14.

Parts common to those in the first to third embodiments are assigned the same reference numerals and overlapping explanations will be omitted. Furthermore, the light-emitting probe is also provided with a structure similar to that of this detection probe 400d, and therefore explanations thereof will be omitted. Here, FIG. 13 is a central longitudinal cross-sectional view of the detection probe. FIG. 14 is a perspective view of the detection probe seen from the top surface.

In FIG. 13, one feature of the detection probe 400d according to this fourth embodiment lies in that this detection probe 400d is constructed of a detection probe mounting section 450d attached to an opening 202 of a probe holder 200 and a detection probe unit 410d housed in a main unit storage section 459d of the detection probe mounting section 450d and this detection probe unit 410d is provided in a manner pivotable with respect to the main unit storage section 459d and in such a way that the amount of protrusion toward the examinee is adjustable.

That is, the detection probe mounting section 459d according to this embodiment is constructed of a cylindrical base 461 provided with the column-shaped main unit storage section 459d inside and a cap 422d to be attached to an upper opening 462 of this base 461. The upper part of the base 461 is open through the upper opening 462 and a lower opening 463 having a smaller diameter than that of the upper opening 462 is formed of a ring projection 466 protruding inward at the bottom.

The cap 422d is provided with a coupling member 423d connected to one top end of the base 461 on one side and also provided with a mounting coupling section 465 attached to a protruding mounting section 464 attached to the other top end of the base 461 on the other side. This coupling member 423d and the mounting coupling section 465 are made of rubber or a flexible resin material. Furthermore, a connection receiving section 454d is further provided inside the cap 422d and this connection receiving section 454d is connected to a signal line 201 of the probe holder 200 through a signal line 423 provided for the coupling member 423d.

On the other hand, a detection probe unit 410 is constructed of a first housing 416d provided with a detection section 411 and a second housing 417d that covers the perimeter of this first housing 416d. The first housing 416d has a columnar appearance and is provided with a main projection 412 at the center of the bottom surface thereof and a connection section 418d on the top surface thereof. The second housing 417d has a "tub-like" appearance that covers the circumferential surface and bottom surface and is provided with an opening 421 that exposes the main projection 412 in the center of the bottom surface thereof and a plurality of sub projections 414 arranged around this opening 421, and the circumferential surface thereof is provided with a ring-shaped positioning flange 425. This positioning flange 425 is formed so as to have a diameter of L7 which has an appropriate space from the inner surface of the main unit storage section 459d to thereby reduce backlash in the horizontal direction.

According to this embodiment, the first housing 416d is inserted from the opening above the second housing 417d first and the detection probe unit 410d can thereby be assembled at a position at which the main projection 412 protrudes from the opening 421 of the detection probe mounting section 450d. This assembled detection probe unit 410d is inserted from the upper opening 462 of the detection probe mounting section 450d into the main unit storage section 459d.

According to this embodiment, the diameter L6 of the detection probe unit 410d is smaller than the inner diameter L5 of the lower opening 463 and the diameter L7 of the positioning flange 425 is larger than the inner diameter L5 of the lower opening 463, and therefore the positioning flange 425 is held by the ring projection 466 so as to expose the lower part of the detection probe unit 410d from the lower opening 463.

The connection receiving section 454d of the cap 422d and the connection section 418 provided for the upper part of the first housing 416d are coupled together and the mounting coupling section 465 provided at the other end of the cap 422d is attached to the mounting section 464 of the detection probe mounting section 450d, and the detection probe unit 410d is thereby held by the cap 422d upper portion of which is attached to the detection probe mounting section 450.

According to this structure, the detection probe unit 410d is attached to the detection probe mounting section 450d through the flexible coupling member 423d coupled with the cap 422d and mounting coupling section 465, and can thereby be moved in the examinee direction L8. With the elasticity of the coupling member 423d and mounting coupling section 465, it is possible to change the posture of the detection probe 410d according to the unevenness of the head of the examinee 50.

Furthermore, according to this embodiment, the detection probe unit 410 is held with the cap 422d protruding above the detection probe mounting section 450d and the coupling member 423d and the mounting coupling section 465 have a flexible strip-shape, and it is thereby possible to rotate the detection probe unit 410d around the central axis Q1 by picking up the cap 422d by fingers or the like. The width of this rotation is not so large, but allows rotation to an extent that it moves the sub projections 414 to sweep aside the hair 52. Moreover, this rotation also allows the detection probe unit 410d to be adjusted to a posture perpendicular to the scalp of the examinee 50.

Fifth Embodiment

Figure 15:
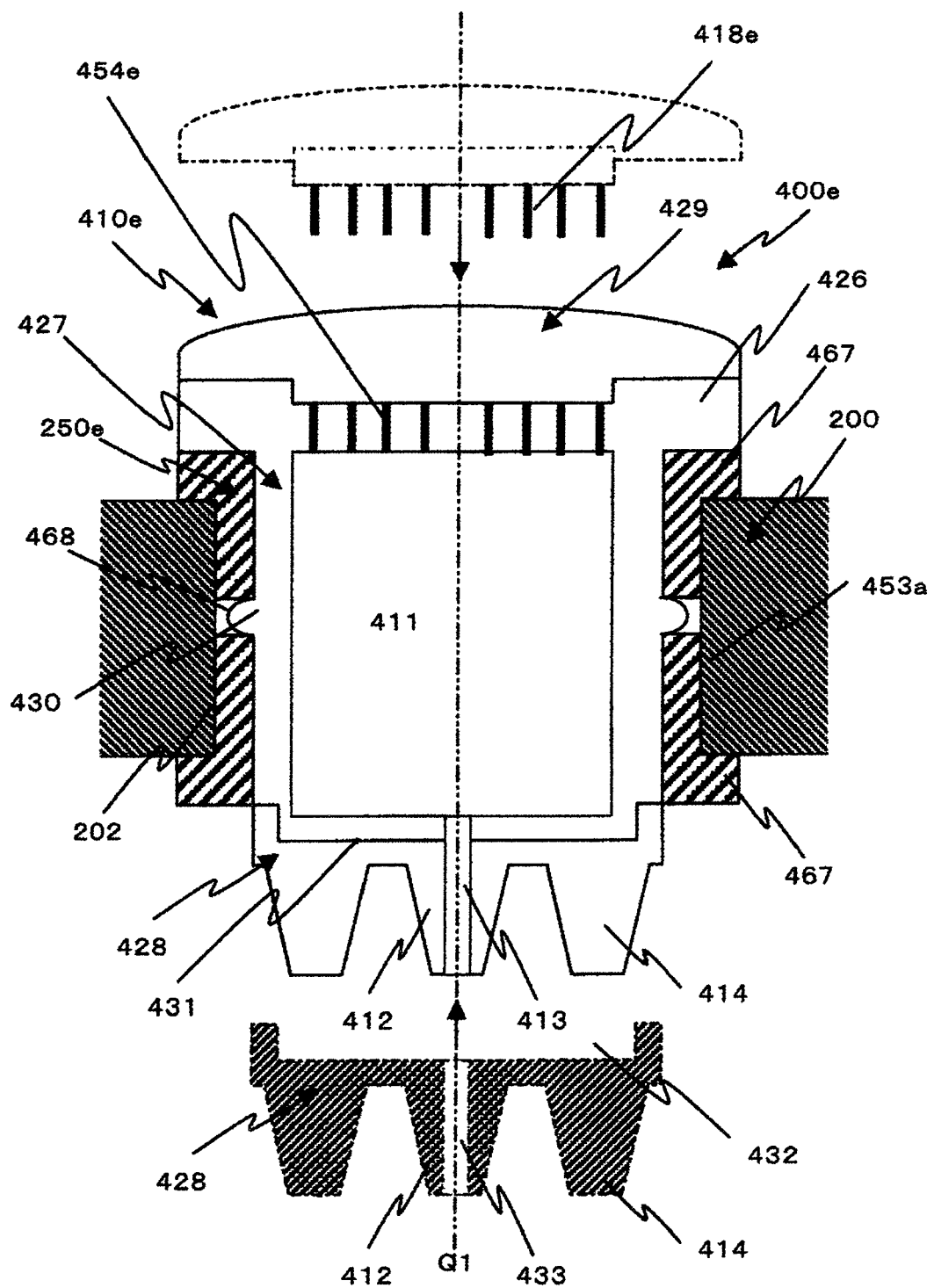
FIG. 15 is a central longitudinal cross-sectional view of a detection probe according to a fifth embodiment.
Figure 16:
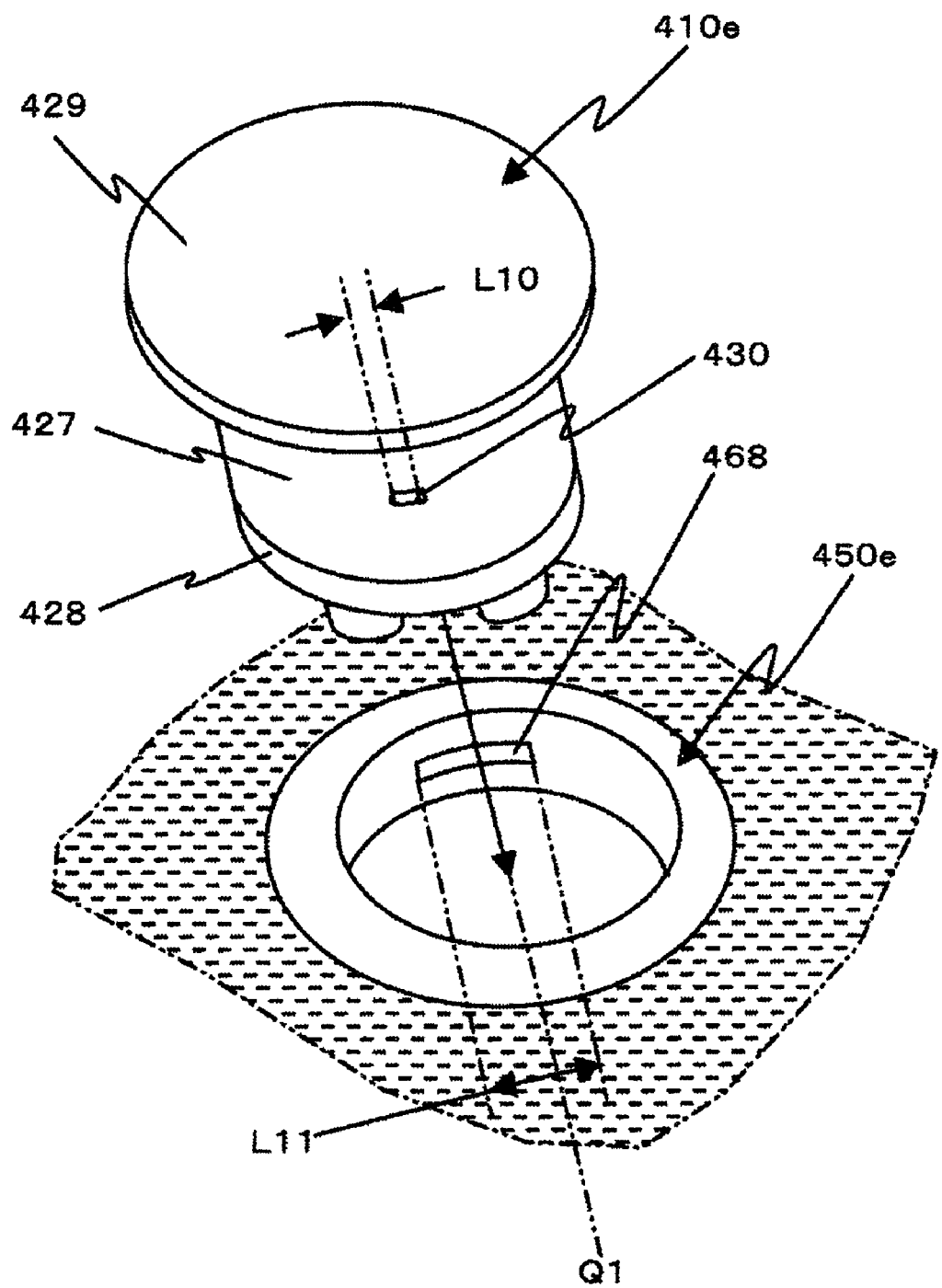
FIG. 16 is a perspective view showing how the detection probe unit according to the fifth embodiment is mounted in the detection probe mounting section.

Next, a detection probe 400e according to a fifth embodiment will be explained in detail with reference to FIG. 15 to FIGS. 18A and 18B. Parts common to those in the first to fourth embodiments are assigned the same reference numerals and overlapping explanations will be omitted. Furthermore, the light-emitting probe is also provided with a structure similar to that of this detection probe 400e, and therefore explanations thereof will be omitted. Here, FIG. 15 is a central longitudinal cross-sectional view of the detection probe. FIG. 16 is a perspective view showing how a detection probe unit is attached to a detection probe mounting section. FIGS. 17A-17D show another arrangement of a main projection and sub projections of the detection probe unit, FIG. 17A is a bottom view, FIG. 17B is a plan view, FIG. 17C is a central cross-sectional view and FIG. 17D is a side view. FIGS. 18A and 18B are bottom views showing another arrangement of sub projections.

In FIG. 15, one feature of a detection probe 400e according to this fifth embodiment lies in that it is configured by including a detection probe mounting section 450e attached to an opening 202 of a probe holder 200 and a detection probe unit 410e which can be attached/detached to/from this detection probe mounting section 450e and which is attached in a manner pivotable around the central axis Q1.

The detection probe mounting section 450e has a ring-shaped appearance provided with a flange 467 protruding outward at the top and bottom ends and mounting engagement holes 468 are provided on both sides of the ring-shaped inner circumferential surface thereof. According to this structure, the detection probe mounting section 450e can be attached to a probe holder 200 with an opening 202 interposed in a recessed part 453a between the upper and lower flanges 467.

The detection probe unit 410e is configured by including a column-shaped main housing 427 provided with a ring-shaped overhang 426 at the top, a contact member 428 attached to the bottom surface of this main housing 427 in a detachable manner and a cap 429 attached to the top surface of this main housing 427 in a detachable manner.

The main housing 427 is provided with a detection section 411 inside and a fiber for detection 413 coupled with this detection section 411 is provided so as to protrude from the center of the bottom surface of the main housing 427. Mounting engagement projections 430 which engage with the above described mounting engagement holes 468 are provided on both sides of the circumferential surface of this main housing 427. Furthermore, the diameter of the ring-shaped overhang 426 is set to substantially the same size of the diameter of the flange 467. Furthermore, a mounting section 431 of a contact member 428 having a stepped perimeter is formed in the lower part of the main housing 427. Furthermore, a connection receiving section 454e connected to the connection section 418e provided for the cap 429 is provided on the top surface of the main housing 427.

On the other hand, the above described contact member 428 is formed of rubber or a flexible resin material and has an appearance with main projection 412 and a plurality of sub projections 414 protruding downward on the bottom surface which is a thin circular base. The plurality of sub projections 414 are arranged on a concentric circle of the main projection 412 in this embodiment, too. A through hole 433 is formed on the central axis of the main projection 412 and a fiber for detection 413 can be inserted into this through hole 433. Furthermore, an engagement recessed part 432 which engages with the mounting section 431 of the main housing 427 is formed on the top surface side of the circular base. According to this contact member 428, the engagement recessed part 432 can be attached to the mounting section 431 using elasticity of resin while passing the fiber for detection 413 through the through hole 433 of the main projection 412.

Furthermore, the cap 429 has a thin disk-shaped outside shape having the same diameter as that of the overhang 426 and is provided with a connection section 418e on one side thereof. A wire (not shown) to be connected to this connection section 418e is drawn out from the other side of the cap 429. This drawn wire is put together with other wires of the detection probe 400e and a light-emitting probe and connected to a biological optical measurement device main unit 10.

In this embodiment, the detection probe mounting section 450e is made of a flexible material and the diameter of the main housing 427 is set such that the detection probe unit 410e (main housing 427) can be inserted with a certain margin with respect to the inner diameter of the detection probe mounting section 450e. Therefore, as shown in FIG. 16, when the main housing 427 provided with the mounting engagement projections 430 on both sides is inserted into the detection probe mounting section 450e, this detection probe mounting section 450e is distorted using elasticity of the resin, making it possible to attach the detection probe mounting section 450e.

When the main housing 427 is attached to the detection probe mounting section 450e, the mounting engagement projections 430 engage with the mounting engagement holes 468 and it is thereby possible to maintain this engagement condition. Furthermore, since the horizontal width L10 of the mounting engagement projection 430 is set to be narrower than the horizontal width L11 of the mounting engagement hole 468, it is possible to rotate the main housing 427 around the central axis Q1 using this wide mounting engagement hole 468.

According to this embodiment, since the contact member 428 provided with the main projection 412 and sub projections 414 can be easily replaced, the contact member 428 can be replaced according to the examinee.

Next, other embodiments of the contact member 428 will be explained with reference to FIGS. 17A-17D and FIGS. 18A and 18B. The structure explained with this contact member 428 is not limited to this embodiment and a similar structure may also be adopted for the first to fourth embodiments explained above.

First, FIGS. 17A-17D show an embodiment of the main projection 412 and sub projections 414 having other shapes. A contact member 428b according to the embodiment in these FIGS. 17A-17D is obtained by forming protuberance 434 at the root of the main projection 412 and sub projections 414 and providing the main projection 412 and sub projections 414 on this protuberance 434. Providing this protuberance 434 makes it possible to adjust the flexibility and strength of the main projection 412 and sub projections 414.

The protuberance 434 can take various forms. For example, in FIG. 17A, the solid line shows a protuberance 434a connecting the roots of the four sub projections 414 seen from the bottom surface with a continuous inward curve. The dotted line shows a protuberance 434b connecting the roots of the four sub projections 414 with a continuous cross-shaped line. Furthermore, the two-dot dashed line shows a protuberance 434c connecting the roots of the four sub projections 414 with a continuous straight line.

Furthermore, the aforementioned embodiments have explained the examples where the four sub projections 414 are provided equidistantly on the concentric circle P1 of the main projection 412, but the present invention is not limited to these in FIGS. 18A and 18B. For example, as shown in FIG. 18A, three sub projections 414 may be provided equidistantly on the concentric circle P1 of the main projection 412. Furthermore, as shown in FIG. 18B, even when four sub projections 414 are provided equidistantly, it is possible to provide sub projections 414a on both sides (in the drawing) on the concentric circle P1 and provide upper and lower (in the drawing) sub projections 414b on a concentric circle P2 having a different diameter. By providing the sub projections 414 on this different concentric circle, it is possible to uniformly sweep aside hair within the projected area of the contact member 428.

Sixth Embodiment

Next, a detection probe 400f according to a sixth embodiment will be explained in detail with reference to FIG. 19 and FIG. 20. Parts common to those in the first to fifth embodiments are assigned the same reference numerals and overlapping explanations will be omitted. Furthermore, the light-emitting probe is also provided with a structure similar to that of this detection probe 400f, and therefore explanations thereof will be omitted. Here, FIG. 19 is a central longitudinal cross-sectional view of the detection probe. FIG. 20 is a perspective view of the detection probe seen from the top surface.

The above described embodiments have explained the cases of embodiments where the probe device 100 and biological optical measurement device main unit 10 are electrically connected, but the present invention is not limited to this embodiment. For example, the present invention is also applicable to a probe device 100 having a structure in which, for example, a light source is provided for the biological optical measurement device main unit 10, light from this light source is supplied to each light-emitting probe 300 through an optical fiber 18, light detected by each detection probe 400 is collected by the biological optical measurement device main unit 10 through the optical fiber 18. FIG. 19 and FIG. 20 show an embodiment adopting the structure of the optical fiber for the fourth embodiment. This structure will be explained hereinafter but this can be applied to the other embodiments explained above.

In FIG. 19, one end of a fiber for detection 413a is exposed from the tip of a main projection 412 and the other end is connected to an optical connector connection section 435 provided in the upper part of a second housing 417d. On the other hand, a cap 422d is provided with an optical connector connection receiving section 469 connectable to the optical connector connection section 435. The optical fiber 18 to be connected to the biological optical measurement device main unit 10 is connected to the optical connector connection receiving section 469. It will be effective if the coupling between this optical fiber 18 and the optical connector connection receiving section 469 is made detachable. As for this structure, the same structure may also be adopted for the light-emitting probe.

According to this embodiment, even when the optical fiber 18 is attached, the detection probe unit 410f can be made rotatable, and therefore operations and effects similar to those in the third embodiment can be obtained.

As described above, the probe device according to this embodiment is used for a biological optical measurement device provided with light irradiation means for irradiating light onto a surface of a living body and light detection means for detecting intensity of light passing through the inside of the living body and emerging from the surface of the living body, including a plurality of light irradiation probe units provided with light irradiation means at a tip thereof, a plurality of light detection probe units provided with light detection means at a tip thereof, a probe support unit which holds a grid-shaped array of the mutually neighboring light irradiation probe units and light detection probe units and a main unit support section which supports the light detection probe unit and the light irradiation probe unit at predetermined positions of the probe support body, wherein the light detection probe unit and the light irradiation probe unit are provided with a main projection formed so as to protrude on the surface side of the living body and a plurality of sub projections arranged around the main projection, the main projection is provided with light communication means for communicating the light irradiation means or the light detection means on an axial core thereof and the main unit support section supports the sub projections to the probe support body in a manner rotatable around the axial core of the light communication means.

In this case, three or more sub projections may be arranged equidistantly on a concentric circle of the main projection. Furthermore, the light detection probe unit and the light irradiation probe unit may be provided with a first housing provided with the main projection and a second housing provided with the sub projections and the second housing may be supported in a manner rotatable with respect to the first housing. Furthermore, the first housing may be provided with connection means for electrically connecting the light irradiation means or the light detection means with the main unit support body section or optically or electrically connecting with an outside device. Moreover, the light detection probe unit and the light irradiation probe unit may also be attached to the main unit support section in a manner detachable therefrom. Furthermore, the sub projection may be mutually coupled via a base plate and the sub projections coupled through the base plate may be attached to the light detection probe unit or the light irradiation probe unit in a manner detachable therefrom. In addition, the second housing may also be attached to the first housing in a manner detachable therefrom.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A probe device for optically measuring a condition of an organism, comprising:
   a light emitter for emitting a light to proceed into the organism through a surface of the organism, and
   a light sensor for measuring an intensity of the light proceeding from the surface through the organism and emitted from the surface to reach the light sensor,
   wherein the probe device further comprises a plurality of light emitting probe bodies having respective front ends on each of which the light emitter is arranged, a plurality of light sensor probe bodies having respective front ends each of which the light sensor is arranged, a probe supporting body holding thereon the light emitting probe bodies and the light sensor probe bodies, and body supporting members for supporting the light emitting probe bodies and the light sensor probe bodies on respective positions on the probe supporting body,
   wherein each of the light sensor probe bodies has a main protrusion protruding to face to the surface so that the main protrusion is supported by the surface, and at least two sub-protrusions protruding to face to the surface and arranged around the main protrusion,
   the main protrusion includes a light transmitting member optically connected to the light sensor and arranged on a longitudinal axis of the main protrusion, and
   the body supporting members support the light sensor probe bodies on the probe supporting body in such a manner that the sub-protrusions is adapted to orbit around the main protrusion.

2. The probe device according to claim 1, wherein the sub-protrusions are arranged along an imaginary circle surrounding the main protrusion at even circumferential intervals.

3. The probe device according to claim 1, wherein each of the light sensor probe bodies includes a first chassis forming the main protrusion and a second chassis forming the sub-protrusions, and the second chassis is supported by the first chassis in a rotatable manner.

4. The probe device according to claim 3, wherein the first chassis has an electric connection member connecting electrically one of the light emitter and the light sensor to corresponding one of the body supporting members.

5. The probe device according to claim 3, wherein the first chassis has a connection member connecting the light sensor to an external device in at least one of optical manner and electrical manner.

6. The probe device according to claim 1, wherein the light emitting probe bodies and the light sensor probe bodies are detachably attached to the body supporting members.

7. The probe device according to claim 3, wherein the light emitting probe bodies and the light sensor probe bodies are detachably attached to the body supporting members.

8. The probe device according to claim 1, wherein the sub-protrusions are connected to each other through a base plate, and the base plate is detachably attached to the corresponding light sensor probe bodies.

9. The probe device according to claim 3, wherein the sub-protrusions are connected to each other through a base plate, and the base plate is detachably attached to the corresponding light sensor probe bodies.

10. The probe device according to claim 2, wherein the light emitting probe bodies and the light sensor probe bodies form a grid-like arrangement so that each of the light emitting probe bodies and respective at least one of the light sensor probe bodies are adjacent to each other.

11. The probe device according to claim 3, wherein the light emitting probe bodies and the light sensor probe bodies form a grid-like arrangement so that each of the light emitting probe bodies and respective at least one of the light sensor probe bodies are adjacent to each other.

12. The probe device according to claim 3, wherein the second chassis is detachably attached to the first chassis.

13. The probe device according to claim 4, wherein the second chassis is detachably attached to the first chassis.

14. The probe device according to claim 5, wherein the second chassis is detachably attached to the first chassis.

15. The probe device according to claim 2, wherein each of the light sensor probe bodies includes a first chassis forming the main protrusion and a second chassis forming the sub-protrusions, and the second chassis is supported by the first chassis in a rotatable manner.

16. The probe device according to claim 2, wherein the sub-protrusions comprise a number of protrusions which is not less than 3 are arranged along the imaginary circle surrounding the main protrusion at the even circumferential intervals.

17. A probe device for optically measuring a condition of an object, comprising:
    a light emitter for emitting a light to proceed into the object through a surface of the object, and
    a light sensor for measuring an optical condition of the light proceeding from the surface through the object and subsequently emitted from the surface to reach the light sensor, and
    a body holding thereon at least one of the light emitter and the light sensor,
    wherein the body includes at least one main protrusion protruding to face to the surface at a front end of the at least one main protrusion so that the front end of the at least one main protrusion is adapted to be supported by the surface, through which front end the light passes between the surface and the at least one of the light emitter and the light sensor, and at least two sub-protrusions protruding to face to the surface at respective front ends of the at least two sub-protrusions, and
    the at least two sub-protrusions are arranged around the at least one main protrusion and are rotatable with respect to the at least one main protrusion so that the front ends of the at least two sub-protrusions are adapted to orbit around the front end of the at least one main protrusion and of to rotate with respect to the surface when the at least one main protrusion is supported at the front end thereof by the surface.

18. The probe device according to claim 17, wherein a positional relationship between the at least two sub-protrusions is fixed.

* * * * *